US011351272B2

(12) United States Patent
Alexander et al.

(10) Patent No.: US 11,351,272 B2
(45) Date of Patent: Jun. 7, 2022

(54) STABLE GENE TRANSFER TO PROLIFERATING CELLS

(71) Applicants: The Sydney Children's Hospitals Network (Randwick and Westmead) (Incorporating the Royal Alexandra Hospital for Children, Westmead (AU); Children's Medical Research Institute, Westmead (AU); Mount Sinai Hospital, Toronto (AU)

(72) Inventors: Ian Alexander, Middle Dural (AU); Sharon Cunningham, North Parramatta (AU); Andras Nagy, Toronto (CA)

(73) Assignees: THE SYDNEYCHILDREN'S HOSPITALS NETWORK (RANDWICK AND WESTMEAD) (INCORPORATING THE ROYAL ALEXANDRA HOSPITAL FOR CHILDREN), Westmead (AU); CHILDREN'S MEDICAL RESEARCH INSTITUTE, Toronto (CA); MOUNT SINAI HOSPITAL, Toronto (CA)

(*) Notice: Subject to any disclaimer, the term of this patent is extended or adjusted under 35 U.S.C. 154(b) by 408 days.

(21) Appl. No.: 16/450,591

(22) Filed: Jun. 24, 2019

(65) Prior Publication Data
US 2020/0016278 A1    Jan. 16, 2020

Related U.S. Application Data

(63) Continuation of application No. 15/127,743, filed as application No. PCT/AU2015/050125 on Mar. 23, 2015, now abandoned.

(51) Int. Cl.
| | |
|---|---|
| A61K 48/00 | (2006.01) |
| C12N 15/86 | (2006.01) |
| C12N 9/00 | (2006.01) |
| C12N 9/10 | (2006.01) |
| C12N 9/12 | (2006.01) |
| C12N 9/14 | (2006.01) |

(52) U.S. Cl.
CPC ........ *A61K 48/0066* (2013.01); *A61K 48/005* (2013.01); *A61K 48/0041* (2013.01); *C12N 9/1018* (2013.01); *C12N 9/1241* (2013.01); *C12N 9/14* (2013.01); *C12N 9/93* (2013.01); *C12N 15/86* (2013.01); *C12Y 201/03003* (2013.01); *C12Y 207/07* (2013.01); *C12Y 306/03044* (2013.01); *C12Y 603/04005* (2013.01); *C12N 2750/14143* (2013.01); *C12N 2800/90* (2013.01); *C12N 2840/007* (2013.01)

(58) Field of Classification Search
None
See application file for complete search history.

(56) References Cited

U.S. PATENT DOCUMENTS

2017/0216456 A1    8/2017   Alexander et al.

OTHER PUBLICATIONS

Hackett, et al. (2010) "A Transposon and Transposase System for Human Application", Molecular Therapy, 18(4): 674-83. (Year: 2010).*
Dagli, et al. (2004) "Delayed liver regeneration and increased susceptibility to chemical hepatocarcinogenesis in transgenic mice expressing a dominant-negative mutant of connexin32 only in liver", Carcinogenesis, 25(4): 483-92. (Year: 2004).*
Bire, et al., "Exogenous mRNA delivery and bioavailability in gene transfer mediated by piggyBac transposition", BMC Biotechnology 13(75), 16 pages (2013).
Cooney, A, et al., "Hybrid Nonviral/Viral Vector Systems for Improved piggyBac DNA Transposon In Vivo Delivery", Molecular Therapy 23(4), 667-674 (2015).
Cunningham, S, et al., "AAV2/8-mediated Correction o fOTC Deficiency is Robust in Adult but not Neonatal Spfash Mice", Molecular Therapy 17(8), 1340-1346 (2009).
Cunningham, S, et al., "Modeling Correction of Severe Urea Cycle Defects in the Growing Murine Liver Using a Hybrid Recombinant Adeno-Associated Virus/piggyBac Transposase Gene Delivery System", Hepatology 62, 417-428 (2015).
Doherty, J, et al., "Hyperactive piggyBac Gene transfer in Human Cells and In Vivo", Human Gene Therapy 23, 311-329 (2012).
Izsvak, Z, "Sleeping Beauty Transposition: Biology and Applications for Molecular Therapy", Molecular Therapy 9 (2), 147-156 (2004).
Kok, C, et al., "Adeno-associated Virus-mediated Rescue of Neonatal Lethality in Argininosuccinate Synthetase-deficient Mice", Molecular Therapy 21(10), 1823-1831 (2013).
Linden, R, "Gene therapy gets the Beauty treatment", Nature Biotechnology 20, 987-988 (2002).
Lipshutz, G, "In Vtero Delivery of Adeno-Associated Viral Vectors: Intraperitoneal Gene Transfer Produces Long-Term Expression", Molecular Therapy 3(3), 284-292 (2001).
Lung, M, et al., "The Use of a Human Papillomavirus 18 Promoter for Tissue-Specific Expression in Cervical Carcinoma Cells", Cellular & Molecular Bilogy Letters 16, 477-492 (2011).

(Continued)

*Primary Examiner* — Robert M Kelly
(74) *Attorney, Agent, or Firm* — Viksnins Harris Padys Malen LLP

(57) ABSTRACT

Provided herein are methods for facilitating or inducing stable transgene integration and expression in a proliferating cell, comprising administering to the cell (i) a recombinant AAV (rAAV) vector comprising the transgene flanked by transposon-derived inverted terminal repeat sequences, which sequences are in turn flanked by AAV-derived inverted terminal repeat regions, and (ii) a source of a transposase that recognises said transposon-derived inverted terminal repeat sequences and directs the genomic integration of the transgene into the genome of the proliferating cell. Also provide are methods and transgene delivery systems for the treatment or prevention of diseases affecting, associated with or characterised by proliferating cells.

9 Claims, 8 Drawing Sheets
Specification includes a Sequence Listing.

(56) References Cited

OTHER PUBLICATIONS

Luo, W., et al., "Development of the hybrid Sleeping Beauty-baculovirus vector for sustained gene expression and cancer therapy", Gene Therapy 19, 844-851 (2012).
Markusic, D., et al., "Liver-Directed Adeno-Associated Viral Gene Therapy for Hemophilia", J Genet Syndr Gene Ther S1:009, 9 pages (2012).
Moldt, B., et al., "Comparative Genomic Integration Profiling of Sleeping Beauty Transposons Mobilized with High Efficacy from Integrase-defective Lentiviral Vectors in Primary Human Cells", Molecular Therapy 19(8), 1499-1510 (2011).
Moscioni, D., et al., "Long-Term Correction of Ammonia Metabolism and Prolonged Survival in Ornithine Transcarbamylase-Deficient Mice Following Liver-Directed Treatment with Adeno-associated Virals Vectors", Molecular Therapy 14(1), 25-33 (2006).
Muck-Hausl, M., "Genetic engineering of adenoviral vectors for improved therapeutic applications", Dissertation, Department of Biochemistry at LMU Munich, 162 pages (2011).
Nakanishi, H., et al., "piggyBac Transposon-mediated Long-term Gene Expression in Mice", Molecular Therapy 18 (4), 707-714 (2010).
Patent Cooperation Treaty, International Searching Authority, Search Report and Written Opinion for PCT/AU2015/050125, 10 pages, dated Apr. 29, 2015.
Sands, M., "AAV-Mediated Liver-Directed Gene Therapy", Methods in Molecular Biology 807, (Chapter 6) 141-157 (2011).
Siew, S., et al., "A Novel, Hybrid Recombinant AAV-piggyBac Transposon Vector Permits Robust Long-Term Phenotype Correction of the Progressive Familial Intrahepatic Cholestasis Type 3 Mouse Model In Vivo", Journal of Hepatology 60, 0136, pp. S57-S58 (2014).
Siew, S., et al., "Liver Fibrosis Impedes Recombinant Adeno-Associated Viral Vector Transduction in Abcb4-/-Mice: Implications for Designing Gene Therapy Strategies Toward Chronic Cholestatic Liver Disease", Hepatology 56(4) Supp, 1285, p. 801A (2012).
Van Til, N., et al., "Alteration of viral lipid composition by expression of the phospholipid floppase ABCB4 reduces HIV vector infectivity", Retrovirology 5(14), 9 pages (2008).
Wilbur, A., et al., "RNA as a Source of transposase for Sleeping beauty-Mediated Gene Insertion and Expression in Somatic Cells and Tissues", Molecular Therapy 13(3), 625-630 (2006).
Zhang, W., et al., "Hybrid AAV/transposase vectors for somatic integration in human cells based on the hyperactive Sleeping Beauty transposase SB100X", European Society of Gene and Cell Therapy Conference, Abstract P282, A152, 2 pages (Oct. 25-29, 2012).
Zhang, W., et al., "Hybrid Adeno-Associated Viral Vectors Utilizing Transposase-Mediated Somatic Integration for Stable Transgene Expression in Human Cells", PLoS One 8(10), e76771, 17 pages (2013).
Cunningham, S., et al., "AAV-Mediated Gene Delivery to the Mouse Liver", Methods Mol Biol 1937, 213-219 (2019).
Ginn, S., et al., "Efficient in vivo editing of OTC-deficient patient-derived primary human hepatocytes", JHEP Reports, https://doi.org/10.1016/j.jhepr.2019.100065, 12 pages (2020).
La, Q., et al., "Use of a Hybrid Adeno-Associated Viral Vector Transposon System to Deliver the Insulin Gene to Diabetic NOD Mice", Cells 9, 2227, 16 pages (2020).
Siew, S., et al., "Prevention of Cholestatic Liver Disease and Reduced Tumorigenicity in a Murine Model of PFIC Type 3 Using Hybrid AAV-piggyBac Gene Therapy", Hepatology 70, 2047-2061 (2019).

\* cited by examiner

Figure 6
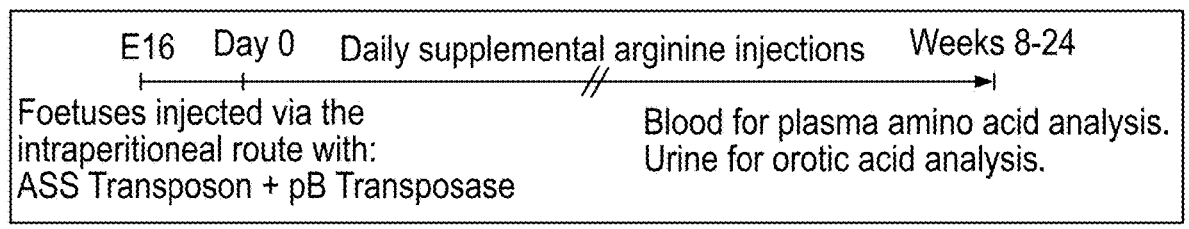
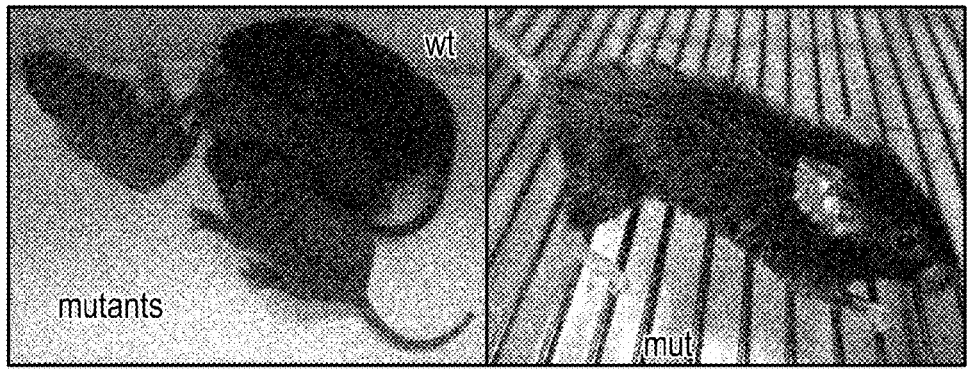
FIG. 7A
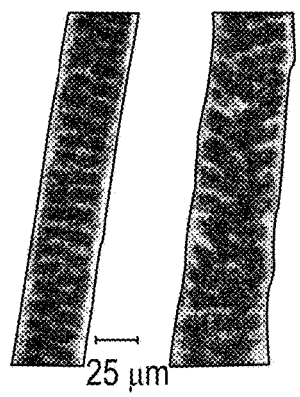
FIG. 7B
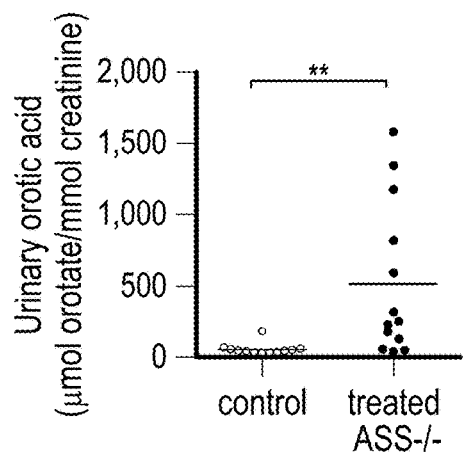
FIG. 7C

Figure 8
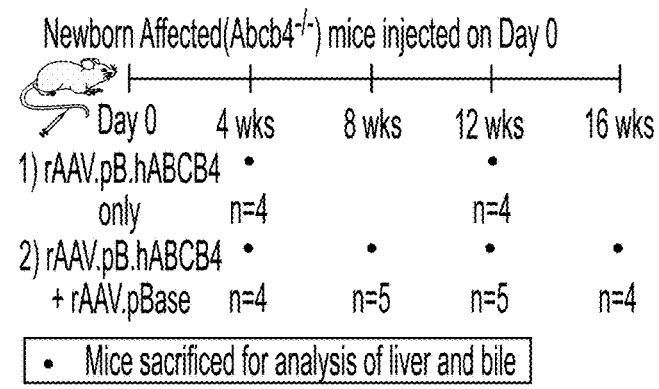
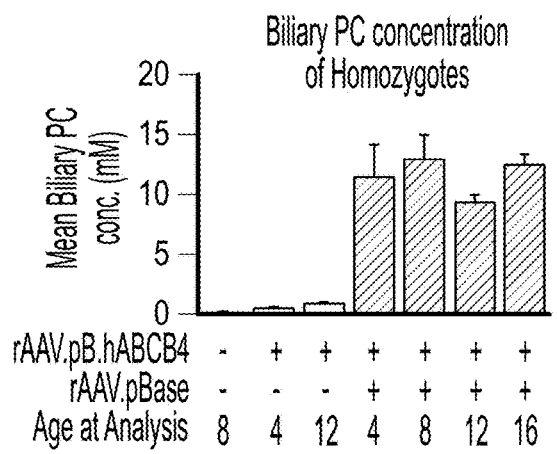
FIG. 9A
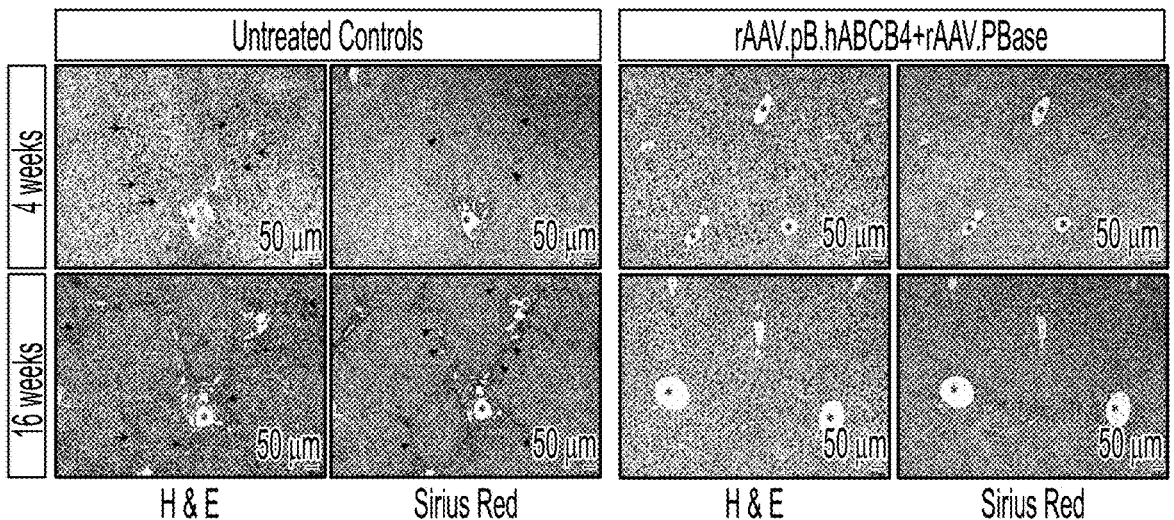
FIG. 9B

STABLE GENE TRANSFER TO PROLIFERATING CELLS

CROSS-REFERENCE TO RELATED APPLICATION(S)

This applications a continuation of U. S. Application Ser. No. 15/127,743, filed Sep. 20, 2016, now abandoned, which is a 35 U. S. C. § 371 U.S. National Phase Application of International Application No. PCT/AU2015/050125, filed Mar. 23, 2015, the disclosure of which is incorporated by reference, and claims priority to Australian Application No. 2014901004, filed Mar. 21, 2014.

TECHNICAL FIELD

The present invention relates generally to methods for stably integrating and expressing transgenes in proliferating cells. The invention also relates to methods and vector systems for the treatment of genetic diseases associated with, or affecting, proliferating cells, organs or tissues.

BACKGROUND ART

Adeno-associated virus (AAV) is a parvovirus having a single-stranded DNA genome. The AAV genome is relatively simple, containing two open reading frames (ORFs) flanked by short inverted terminal repeats (ITRs). The ITRs contain, inter alia, cis-acting sequences required for virus replication, rescue, packaging and integration. The integration function of the ITR permits the AAV genome to integrate into a cellular chromosome after infection.

Recombinant AAV vectors have been shown to be able to transduce a wide range of different cell types, such as hematopoietic cells, epithelial cells and neurons. Interest in AAVs as vectors for gene therapy results from several advantageous features of their biology. These include their ability to transduce non-dividing and dividing cells, their capacity for stable genetic transformation, and the fact that AAVs do not cause disease (and low immunogenicity) in humans. The integration of AAV vectors into the genome of target cells enables long term transgene expression in transduced cells. At least twelve different AAV serotypes have been identified and well characterized, including AAV2 and AAV8, the most widely employed in constructing recombinant AAV vectors for gene transfer and gene therapy applications.

Notwithstanding the attractive aspects of AAV-based vectors, a significant challenge, as yet not overcome, to their widespread use is maintaining stable levels of therapeutically effective transgene expression in proliferating cells such as in the juvenile liver and in bone marrow. For example, despite high efficiency of transduction of neonatal mouse hepatocytes by recombinant AAV vectors, episomal vectors are rapidly lost and eliminated within 2 weeks, and stable transgene expression is observed in only a very small proportion (about 5-10%) of cells (Cunningham et al., 2008, *Molecular Therapy* 16:1081-1088). This significantly hampers the further development of AAV-based gene therapy approaches to the treatment of, for example, genetic liver diseases, and in particular paediatric liver diseases.

There remains a need for vector systems and methods to increase stable transgene expression in proliferating cells to therapeutically effective levels so as to enable the development of gene therapy approaches to treating diseases associated with cellular proliferation such as cancer, and diseases affecting proliferating cells, organs and tissues, such as paediatric liver diseases.

SUMMARY OF THE INVENTION

According to a first aspect the present invention provides a method for facilitating or inducing stable transgene expression in a proliferating cell, the method comprising administering to the cell: (i) a recombinant AAV (rAAV) vector comprising the transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of the proliferating cell.

Typically the genomic integration of the transgene into the genome of the proliferating cell in accordance with the present method facilitates or induces the stable transgene expression.

A second aspect of the invention provides a method for stably integrating a transgene into the genome of a proliferating cell, the method comprising administering to the cell: (i) a recombinant AAV (rAAV) vector comprising the transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of the proliferating cell.

Typically the stable integration of the transgene into the genome of the proliferating cell facilitates or induces the stable expression of the transgene in the cell.

The method of the first or second aspect may be employed to treat or prevent a disease in a subject, wherein the stable genomic integration and expression of the transgene is desired and beneficial in the treatment or prevention of the disease. Typically the disease is a disease affecting, or associated with, proliferating cells.

Typically the disease is a genetic disease. The disease may be associated with the deficiency of one or more gene products in the proliferating cell, typically wherein expression of the transgene normalises production and activity of the deficient gene product. In one embodiment the disease may be a paediatric liver disease. The paediatric liver disease may be selected from OTC deficiency, ASS deficiency and progressive familial intrahepatic cholestasis. The progressive intrahepatic cholestasis may be progressive familial intrahepatic cholestasis type 3. In alternative embodiments, the disease may be cancer or a bone marrow disease.

In an embodiment, wherein the disease is OTC deficiency, the transgene typically comprises a polynucleotide encoding ornithine transcarbamylase (OTC). In an embodiment, wherein the disease is ASS deficiency, the transgene typically comprises a polynucleotide encoding argininosuccinate synthetase (ASS). In an embodiment, wherein the disease is progressive familial intrahepatic cholestasis type 3, the transgene typically comprises a polynucleotide encoding ATP-binding cassette subfamily B member 4 (ABCB4).

A third aspect of the invention provides a method for treating or preventing a disease of, affecting, or associated with, a proliferating cell, comprising administering to a subject in need thereof (i) a recombinant AAV (rAAV) vector comprising a transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of the proliferating cell, wherein said administration results in the stable integration and expression of the transgene to thereby treat the disease.

A fourth aspect of the invention provides a transgene delivery and expression system for inducing stable transgene expression in a proliferating cell, wherein the system comprises (i) a recombinant AAV (rAAV) vector comprising the transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of the proliferating cell.

A fifth aspect of the invention provides a transgene delivery and expression system for treating or preventing a disease of, affecting, or associated with, a proliferating cell, wherein the system comprises (i) a recombinant AAV (rAAV) vector comprising the transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of the proliferating cell.

A sixth aspect of the invention provides the use of (i) a recombinant AAV (rAAV) vector comprising a transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of a proliferating cell, in the manufacture of a medicament for inducing stable transgene expression in a proliferating cell.

A seventh aspect of the invention provides the use of (i) a recombinant AAV (rAAV) vector comprising a transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of a proliferating cell, in the manufacture of a medicament for treating or preventing a disease of, affecting, or associated with, a proliferating cell.

In accordance with the above aspects, typically the disease is a genetic disease. The disease may be associated with the deficiency of one or more gene products in the proliferating cell, typically wherein expression of the transgene normalises production and activity of the deficient gene product. In one embodiment the disease may be a paediatric liver disease. The paediatric liver disease may be selected from OTC deficiency, ASS deficiency and progressive familial intrahepatic cholestasis. The progressive intrahepatic cholestasis may be progressive familial intrahepatic cholestasis type 3. In alternative embodiments, the disease may be cancer or a bone marrow disease.

In an embodiment, wherein the disease is OTC deficiency, the transgene typically comprises a polynucleotide encoding ornithine transcarbamylase (OTC). In an embodiment, wherein the disease is ASS deficiency, the transgene typically comprises a polynucleotide encoding argininosuccinate synthetase (ASS). In an embodiment, wherein the disease is progressive familial intrahepatic cholestasis type 3, the transgene typically comprises a polynucleotide encoding ATP-binding cassette subfamily B member 4 (ABCB4).

The embodiments and associated disclosure below relate to each of the aspects described above.

The transgene may be any gene the expression of which it is desirable to induce in the proliferating cell. The transgene may be foreign to the proliferating cell. The transgene may be a gene the expression of which is absent or reduced in the proliferating cell in the absence of introduction of the transgene.

In an embodiment the transgene and flanking transposon-derived inverted terminal repeat sequences form a transposon-transgene cassette, optionally comprising one or more further sequences or genetic elements including, for example, a promoter, enhancer, post-regulatory element and/or polyadenylation signal sequence. The cassette may be packaged in a suitable AAV capsid.

Typically the transgene is operably linked to a suitable promoter. The promoter may be a tissue-specific promoter. In an embodiment the promoter is a liver-specific promoter. In an exemplary embodiment the liver-specific promoter is the human alpha-1 antitrypsin promoter.

The transposase is provided to the proliferating cell in any form that allows transient expression of the transposase in the cell. Typically the transposase is administered to the proliferating cell in the form of a polypeptide, or a polynucleotide encoding the transposase. The polynucleotide may be a gene or mRNA. In a particular embodiment, the transposase is provided to the proliferating cell using a second rAAV vector comprising a polynucleotide encoding the transposase, optionally operably linked to a suitable promoter, and optionally flanked by AAV-derived inverted terminal repeat regions. The promoter may be a tissue-specific promoter. In an embodiment the promoter is a liver-specific promoter. In an exemplary embodiment the liver-specific promoter is the human alpha-1 antitrypsin promoter.

In particular embodiments the AAV sequences used in the rAAV vectors may be derived from AAV2 and/or AAV8. Where the vector genome is encapsidated, any capsid capable of encapsidating an AAV genome may be employed.

In an exemplary embodiment the transposase is the piggyBac transposase, and the transposon-derived inverted terminal repeat sequences are derived from the piggyBac transposon.

The proliferating cell may be a rapidly proliferating cell. In particular embodiments, the cell is a hepatocyte from a neonatal or juvenile liver or a bone marrow cell. The proliferating cell may be a disease cell, such as a cancer cell.

BRIEF DESCRIPTION OF THE DRAWINGS

Embodiments of the invention are described herein, by way of example only, with reference to the accompanying drawings.

FIG. 1A. PiggyBac transposase vector. FIG. 1B. EGFP reporter vector with either the full length (TRSI, TRSII) or short (TRS I, TRS II)piggyBac terminal resolution sites (TRS). FIG. 1C. Transposon-donor plasmids expressing either murine OTC, murine ASS or human ABCB4. LSP1, liver specific ApoE/hAAT enhancer/promoter; LP1*, shortened version of LSP1; ITR, AAV2 inverted terminal repeat regions; PRE, post-transcriptional regulatory element; pA, polyadenylation signal. Component nucleotide sequences are defined in Table 1 and sequences are provided in SEQ ID Nos:1 to 18 of the Sequence Listing. Vector construct sequences are further described in Example 1 and sequences provided in SEQ ID Nos:19 to 23 of the Sequence Listing.

FIG. 3A. Representative images of liver sections showing widespread and numerous EGFP-positive hepatocytes following concomitant delivery of rAAV-encoded transposase to the newborn (1-2 days) mouse liver compared with EGFP transposon vector alone. Scale bar=50 μm. FIG. 3B. Fluorometric analysis of liver lysates showing higher levels of EGFP expression in 4 week old mice receiving transposon-encoded EGFP in the presence of piggyBac transposase (n=4) than transposon alone (n=4). FIG. 3C. Quantitation of vector genome (vg) copy number per diploid liver cell at 4 weeks of age with transposon-encoded EGFP (full length TRS vector) in the presence of piggyBac transposase. FIG. 3D. Relative EGPF mRNA and FIG. 3E. protein expression per vector genome (vg) copy number (arbitrary units) at 4 weeks of age with transposon-encoded EGFP (full length TRS vector) in the presence of piggyBac transposase. FIG. 3F. Fluorometric quantitation of EGFP in liver lysates with EGFP transposon rAAV alone (short TIR) (n=3 male, n=3 female) or in combination with the piggyBac transposase rAAV (n=3 male, n=3 female). FIG. 3G. Quantitation of vector genome (vg) copy number per diploid liver cell with EGFP transposon rAAV alone (short TIR) or in combination with the piggyBac transposase rAAV. FIG. 3H. Relative EGFP protein expression per vector genome copy number (arbitrary units) with EGFP transposon rAAV alone (short TIR) or in combination with the piggyBac transposase rAAV. Dot plots in panels of FIGS. 3C to 3H show mean values. EGFP transposon-encoding vector alone and in combination with the piggyBac transposase-encoding vector are indicated by open and closed dots, respectively. For statistical comparison of two experimental groups, the two-tailed Student's unpaired t-test was used: *P<0.05; P<0.01; *P<0.001.

FIG. 5A. Representative images of liver sections showing widespread OTC activity (dark brown stain) in mice receiving both the OTC-encoding transposon-transgene vector and the piggyBac transposase vector (right panel; 66±5% gene-modified cells), compared with mice that received OTC-encoding transposon-transgene vector alone (left panel; 1±0.2% gene-modified cells). FIG. 5B. Kaplan-Meier survival analysis of mice receiving the OTC-encoding transposon-transgene vector alone or in combination with the piggyBac transposase vector, followed by knockdown of residual endogenous OTC activity at adulthood. FIG. 5C. OTC enzymatic activity in liver lysates presented as fold-difference over wild-type (wt). FIG. 5D. Quantitation of vector genome (vg) copy number per diploid liver cell. FIG. 5E. Relative mOTC mRNA and FIG. 5F. protein expression per vector genome copy number (arbitrary units). Dot plots in panels of FIGS. 5C to 5F show mean values. OTC transposon-encoding vector alone and in combination with the piggyBac transposase-encoding vector are indicated by open and closed dots, respectively. For statistical comparison of two experimental groups, the two-tailed Student's unpaired t-test was used: *P<0.05; P<0.01; *P<0.001; **** P<0.0001.

FIG. 6. Experimental design for testing phenotype correction following co-delivery of the ASS-encoding transposon-transgene vector and the piggyBac transposase vector, in the citrullinaemic mouse model of ASS deficiency.

FIGS. 7A-7E. FIG. 7A. ASS-deficient pups treated with ASS-encoding transposon-transgene vector and the piggyBac transposase vector and wild-type litter mate at 10 days of age (left panel), and treated ASS-deficient adult (8 week old) mouse (right panel). FIG. 7B. Microscopic analysis of hair strands from a wild-type (wt) and treated adult mutant (mut) mouse. Scale bar, 25 FIG. 7C. Plasma urinary orotic acid in wild-type/heterozygous (open symbols) and treated mutant adult mice (closed symbols). FIG. 7D. ASS enzyme activity in liver lysate from wild-type (wt) and heterozygous (het) males and females and treated mutant (ASS−/−) adult mice. FIG. 7E. Localisation of ASS protein in liver sections by immunohistochemistry, co-localised with glutamine synthetase (darkest stained cells) to identify the hepatic central veins. Representative histological images from a wild-type control liver (left) and a treated mutant mouse liver (right). Scale bar, 50 Dot plots in panels of FIGS. 7C and 7D show mean values. For statistical comparison of two experimental groups, the two-tailed Student's unpaired t-test was used: P<0.01; **P<0.0001.

FIG. 8. Experimental design for testing phenotype correction following co-delivery of the hABCB4-encoding transposon-transgene vector and the piggyBac transposase vector, in mouse model of progressive familial intrahepatic cholestasis type 3 (PFIC3).

FIGS. 9A-9B. FIG. 9A. Homozygous neonates (Abcb4$^{−/−}$) that received a single therapeutic injection of rAAV-piggyBac transposon (with short TRS) encoding human ABCB4 (rAAV.pB.hABCB4), co-administered with vector encoding piggyBac tranposase (rAAV.pBase) had stably increased mean biliary phosphatidylcholine (PC) concentrations at 4, 8, 12 and 16 weeks of age, compared to untreated controls and those that did not receive concomitant rAAV.pBase. FIG. 9B. Homozygotes treated at birth had minimal evidence of liver pathology on representative histology images at early (4 weeks) and late (16 weeks) analysis time-points. Portal tracts (marked with asterisks) of treated mice are normal, in contrast with those of untreated controls exhibiting periportal inflammation and features of biliary obstruction. Infiltration of inflammatory cells also extends between portal tracts of untreated controls in the haemotoxylin and eosin (H & E) stained images (arrow) and increased fibrosis bridges portal tracts in Sirius red stained images, most noticeably at 16 weeks in the untreated controls (arrowhead). Scale bar=50 μm.

Figures 1A, 1B, 1C:
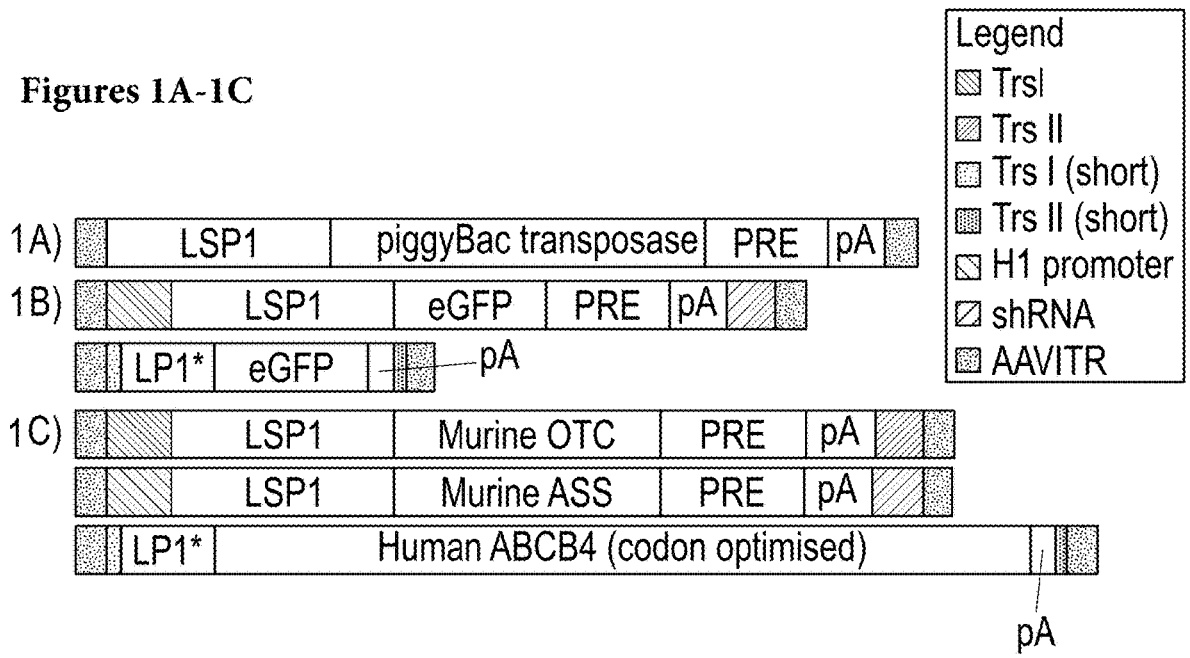
FIGS. 1A-1C. Vector constructs.

The present specification contains nucleotide sequence information prepared using the programme PatentIn Version 3.5, presented herein in a Sequence Listing.

DETAILED DESCRIPTION OF THE INVENTION

Throughout this specification and the claims which follow, unless the context requires otherwise, the word "comprise", and variations such as "comprises" or "comprising", will be understood to imply the inclusion of a stated element, integer or step, or group of elements, integers or steps, but not the exclusion of any other element, integer or step, or group of elements, integers or steps.

The articles "a" and "an" are used herein to refer to one or to more than one (i.e., to at least one) of the grammatical object of the article. By way of example, "an element" means one element or more than one element.

As used herein the term "derived" in the context of an AAV-derived or transposon-derived nucleotide sequence means that the sequence corresponds to, originates from, or otherwise shares significant sequence homology with a sequence from an AAV or a transposon. Those skilled in the art will also understand that by being "derived" from an AAV or transposon, the sequence need not be physically constructed or generated from a particular AAV or transposon, but may be chemically synthesised or generated by other molecular biology techniques known in the art.

As used herein, the term "transgene" refers to exogenous DNA or cDNA encoding a gene product. The gene product may be an RNA, peptide or protein. In addition to the coding region for the gene product, the transgene may include or be associated with one or more elements to facilitate or enhance expression, such as a promoter, enhancer(s), response element(s), reporter element(s), insulator element(s), polyadenlyation signal(s) and/or other functional elements. Embodiments of the invention may utilize any known suitable promoter, enhancer(s), response element(s), reporter element(s), insulator element(s), polyadenlyation signal(s) and/or other functional elements. Suitable elements and sequences will be well known to those skilled in the art. The transgene integrates into the genome of a proliferating cell. The transgene may be foreign to the cell or may represent a gene the expression of which is otherwise absent or reduced in the proliferating cell in the absence of the introduction of the transgene.

It will be understood that as used herein the term "expression" may refer to expression of a polypeptide or protein, or to expression of a polynucleotide or gene, depending on the context. Expression of a polynucleotide may be determined, for example, by measuring the production of RNA transcript levels using methods well known to those skilled in the art. Expression of a protein or polypeptide may be determined, for example, by immunoassay using an antibody(ies) that bind with the polypeptide using methods well known to those skilled in the art.

In the context of this specification, the term "activity" as it pertains to a protein, polypeptide or polynucleotide means any cellular function, action, effect or influence exerted by the protein, polypeptide or polynucleotide, either by a nucleic acid sequence or fragment thereof, or by the protein or polypeptide itself or any fragment thereof.

As used herein the term "effective amount" includes within its meaning a non-toxic but sufficient amount of an agent or compound to provide the desired therapeutic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the terms "treating", "treatment", "preventing" and "prevention" and variations thereof refer to any and all uses that remedy a disease or one or more symptoms thereof, prevent the establishment of the disease, or otherwise prevent, hinder, retard, or reverse the progression of the disease or other undesirable symptoms in any way whatsoever. Thus the terms "treating" and "preventing" and the like are to be considered in their broadest context. For example, treatment does not necessarily imply that a patient is treated until total recovery. In conditions which display or a characterized by multiple symptoms, the treatment or prevention need not necessarily remedy, prevent, hinder, retard, or reverse all of said symptoms, but may prevent, hinder, retard, or reverse one or more of said symptoms.

As used herein the term "associated with" when used in the context of a disease "associated with" a proliferating cell means that the disease may result from, result in, be characterised by, or otherwise associated with cellular proliferation. The association between the disease and cellular proliferation may be direct or indirect and may be temporally separated.

The term "subject" as used herein refers to mammals and includes humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Typically the mammal is human or a laboratory test animal. Even more typically, the mammal is a human.

As described and exemplified herein the inventors have generated recombinant AAV vectors and vector systems capable of inducing stable integration and high levels of expression of transgenes in proliferating cells. The inventors have also demonstrated the ability of these vectors and vector systems to correct phenotypes in mouse models of three different diseases of the paediatric liver.

Accordingly, provided herein are methods and vector systems for inducing stable transgene expression in a proliferating cell, the method comprising administering to the cell: (i) a recombinant AAV (rAAV) vector comprising the transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of the proliferating cell.

Also provided herein are methods and vector systems for stably integrating a transgene into the genome of a proliferating cell, the method comprising administering to the cell: (i) a recombinant AAV (rAAV) vector comprising the transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of the proliferating cell.

Also provided herein are methods and vector systems for treating or preventing a disease of, affecting, or associated with, a proliferating cell, comprising administering to a subject in need thereof (i) a recombinant AAV (rAAV) vector comprising a transgene flanked by transposon-derived inverted terminal repeat sequences, which sequences are in turn flanked by AAV-derived inverted terminal repeat regions; and (ii) a source of a transposase that recognises said transposon-derived inverted terminal repeat sequences and directs the genomic integration of the transgene into the genome of the proliferating cell, wherein said administration results in the stable integration and expression of the transgene to thereby treat the disease.

In particular embodiments of the present invention, the proliferating cell may be a liver cell, in particular a cell of a neonatal or juvenile liver, a bone marrow cell and/or a cancer cell. However those skilled in the art will appreciate that the present invention is applicable to any proliferating cell, and thus to any disease of, affecting, or associated with such proliferating cells. Non-limiting examples of paediatric liver diseases that may be treated or prevented in accordance with embodiments of the invention include OTC deficiency, ASS deficiency, progressive familial intrahepatic cholestasis, and genetic or metabolic liver diseases.

The vector systems of the invention may be used to integrate and express any transgene in the genome of a proliferating cell, and the scope of the present disclosure is not to be limited by reference to any particular transgene exemplified herein. The transgene may be any gene the expression of which it is desirable to induce in the proliferating cell. The transgene may be foreign to the proliferating cell. The transgene may be a gene the expression of which is absent or reduced in the proliferating cell in the absence of introduction of the transgene.

Accordingly, methods and vector systems of the invention find application in any circumstance or scenario in which it is desirable to stably integrate and express a transgene in a proliferating cell. Thus applications of the invention as a research tool in the investigation of gene expression, the development of, for example, cell lines and animal models, and alleviating the need to generate transgenic animals, are contemplated, in addition to the application of the invention to the treatment and prevention of diseases of, affecting, or associated with proliferating cells such as those of the neonatal or juvenile liver or bone marrow.

The transposase may be delivered to a proliferating cell in the form of a polypeptide, or a polynucleotide encoding the transposase. In a particular embodiment, the transposase is delivered using a vector comprising a polynucleotide encoding the transposase, optionally flanked by AAV-derived inverted terminal repeat regions. However those skilled in the art will recognise that the transposase may be delivered in any suitable form and by any suitable means so as to allow for expression of the transposase in the cell for a sufficient period of time and in sufficient amount to integrate the transgene or transgene cassette from the first rAAV vector into the genome of the proliferating cell. It will therefore be appreciated that transient expression of the transposase is required to prevent remobilization (excision) of integrated elements. Accordingly, the transposase may be delivered to the cell as mRNA encoding the transposase enzyme, or means of eliminating transposase enzyme from the cell may be employed, although any means of achieving transient transposase expression is contemplated.

Optionally polynucleotides administered to proliferating cells, encoding the transposase and/or the transgene, may be operably linked to a promoter. Thus, typically the vectors of the present invention are expression vectors capable of directing the transcription of the DNA sequence of the polynucleotide contained in the vector. The vector may include other expression control and processing sequences such as, for example, enhancers, internal ribosome entry sites, 2A elements, translation initiation (e.g. Kozak) sequences, polyadenylation signals and transcription termination sequences.

The promoter operably linked to the transposase and/or the transgene may be a "ubiquitous" promoter active in essentially all cells of the host organism (e.g. the beta-actin or cytomegalovirus promoters) or may be a promoter with expression more or less specific to the target cells (albumin promoter). Thus, the promoter may be a tissue-specific promoter that is only (or predominantly) active in cells of the desired tissue or organ. Thus, in particular embodiments the promoter may be one that is active primarily in the hepatic system. The specificity may be absolute or relative. Similarly, the promoter may be specific for particular cell types, including for example hepatocytes, Kupffer cells or endothelial cells. Those of ordinary skill in the art will appreciate that a tissue-specific promoter for use in an AAV vector in accordance with the invention may be selected from any of the known tissue-specific promoters. In an exemplary embodiment a suitable liver-specific promoter is the human alpha-1 antitrypsin promoter.

AAVs of any known serotype may be used in deriving the rAAV vectors of the invention, such as AAV1, AAV2, AAV3, AAV4, AAV5, AAV6, AAV7, AAV8, AAV9, AAV10, AAV11 and AAV12, and subtypes thereof. Exemplary AAVs include AAV2 and AAV8. In exemplary embodiments described herein the AAV inverted terminal repeat sequences are derived from AAV2, and comprise the nucleotide sequences set forth in SEQ ID NO:1 (ITR1) and/or SEQ ID NO:2 (ITR2), or functionally equivalent fragments thereof. The selection of the most appropriate AAV may be based on various factors including for example the target cell or cell type, and the identity or size of the transgene. The skilled addressee can make the selection without undue experimentation.

Those skilled in the art will also appreciate that while exemplified in relation to the piggyBac transposon, the methods and systems of the present invention may employ sequences derived from any suitable transposon. By way of example the transposon may be a member of the piggyBac superfamily or the Tc1/mariner superfamily (including for example the Sleeping Beauty transposon). The most appropriate transposon to be employed may be selected depending on the application of the invention, the target cell or cell type, the identity of the transgene and the disease to be treated or prevented. The skilled addressee can make the selection without undue experimentation. In exemplary embodiments described herein the transposon-transgene vectors comprise terminal repeat sequences derived from the piggyBac transposon, which sequences comprise the nucleotide sequences set forth SEQ ID NO:3, SEQ ID NO:4, SEQ ID NO:5 and/or SEQ ID NO:6, or functionally equivalent fragments thereof. Similarly, the transposase may be the piggyBac transposase encoded by the nucleotide sequence set forth in SEQ ID NO:7, or a variant or derivative thereof.

The various polynucleotide and polypeptide sequences used in the methods and vectors of the invention, including inter alia AAV-derived inverted terminal repeat regions, transposon-derived inverted terminal repeats, transposase sequences and transgene sequences may be natural, recombinant or synthetic and may be obtained by purification from a suitable source or produced by standard recombinant DNA techniques such as those well known to persons skilled in the art, and described in, for example, Sambrook et al., *Molecular Cloning: a Laboratory Manual*, Cold Spring Harbor Laboratory Press (the disclosure of which is incorporated herein by reference).

In embodiments in which a first rAAV vector comprising the transgene and a second vector comprising a polynucleotide encoding the transposase are co-administered to the proliferating cell, the ratio of the first vector to the second vector may be between about 50:1 to about 1:50, between about 40:1 to 1:40, between about 30:1 to 1:30, between about 20:1 to 1:20, between about 10:1 to 1:10 or between about 5:1 to 1:5. In an exemplary embodiment the ratio of the first vector to the second vector is about 10:1.

The present invention contemplates the delivery of vectors and other molecules to proliferating cells by any suitable means. For administration to subjects requiring treatment, vectors and other molecules are typically administered in the form of pharmaceutical compositions, which compositions may comprise one or more pharmaceutically acceptable carriers, excipients or diluents. Such compositions may be administered in any convenient or suitable route such as by parenteral (e.g. subcutaneous, intraarterial, intravenous, intramuscular), oral (including sublingual), nasal or topical routes. In circumstances where it is required that appropriate concentrations of the vectors and molecules are delivered directly to the site in the body to be treated, administration may be regional rather than systemic. Regional administration provides the capability of delivering very high local concentrations of the vectors and molecules to the required site and thus is suitable for achieving the desired therapeutic or preventative effect whilst avoiding exposure of other organs of the body to the vectors and molecules and thereby potentially reducing side effects.

It will be understood that the specific dose level of a composition of the invention for any particular subject will depend upon a variety of factors including, for example, the activity of the specific agents employed, the age, body weight, general health and diet of the individual to be treated, the time of administration, rate of excretion, and combination with any other treatment or therapy. Single or multiple administrations can be carried out with dose levels and pattern being selected by the treating physician. A broad range of doses may be applicable. Considering a patient, for example, from about 0.1 mg to about 1 mg of agent may be administered per kilogram of body weight per day. Dosage regimens may be adjusted to provide the optimum therapeutic response. For example, several divided doses may be administered daily, weekly, monthly or other suitable time intervals or the dose may be proportionally reduced as indicated by the exigencies of the situation.

Examples of pharmaceutically acceptable carriers or diluents are demineralised or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanoyls; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The present invention contemplates combination therapies, wherein vectors and molecules as described herein are coadministered with other suitable agents that may facilitate the desired therapeutic or prophylactic outcome. By "coadministered" is meant simultaneous administration in the same formulation or in two different formulations via the same or different routes or sequential administration by the same or different routes. By "sequential" administration is meant a time difference of from seconds, minutes, hours or days between the administration of the agents. Administration may be in any order.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavor to which this specification relates.

The present invention will now be described with reference to the following specific examples, which should not be construed as in any way limiting the scope of the invention.

EXAMPLES

Example 1—AAV/Transposase Vector Constructs

Transposon-donor vectors and a piggyBac Transposase vector were constructed using the recombinant adeno-associated viral vector (rAAV) system. The hybrid AAV/transposase system was subsequently used (see Examples 2 to 4) to demonstrate phenotype correction in animal models with genetic metabolic disease phenotypes. These included the spf$^{ash}$ mouse model of ornithine transcarbamylase (OTC) deficiency and the citrullinaemic mouse model of argininosuccinate synthetase (ASS) deficiency (both urea cycle disorders), and the PFIC3 mouse model (ABCB4 deficiency) of progressive familial intrahepatic cholestasis. Each of these disease phenotypes presents early in life, in neonates or juveniles.

The coding sequence of piggyBac transposase was amplified by PCR from pCAG-PBase. The piggyBac transposase vector was constructed by inserting the coding region of the piggyBac transposase into a rAAV2 genome under the transcriptional control of a liver-specific promoter (pAAV2-LSP1.EGFP), replacing the EGFP coding sequence to produce pAAV2-LSP1.PBase (FIG. 1A). To construct the transposon-donor vectors, the 5' (313 bp) and 3' (230 bp)piggyBac transposon terminal inverted repeats (TIRs) were amplified by PCR from pPB-CA-GFP (Wolten et al., 2011, *Methods Mol. Biol.* 767:87-103) and inserted into pAAV2-LSP1.EGFP, immediately internal to the AAV2 inverted terminal repeats (ITRs) and flanking the transgene cassette. The resulting vector construct was designated pAAV2-LSP1.EGFP-TIR (FIG. 1B).

The piggyBac terminal repeat sequences used were either full length (TRS I, 313 bp, SEQ ID NO:3; and TRS II, 230 bp, SEQ ID NO:4) or shortened forms (TRS I, 67 bp, SEQ ID NO:5; and TRS II, 40 bp, SEQ ID NO:6). The genes expressed by the transposon-donor transgene cassettes included enhanced green fluorescent protein (EGFP) (FIG. 1B), murine ornithine transcarbamylase (OTC), murine argininosuccinate synthetase (ASS) and human ATP-binding cassette subfamily B member 4 (ABCB4) (FIG. 1C). To produce the therapeutic transposon vector constructs pAAV2-LSP1.mOTC-TIR (Example 3) and pAAV2-LSP1.mASS-TIR (Example 4), the EGFP cDNA in pAAV2-LSP1.EGFP-TIR was replaced with the cDNA for either murine ornithine transcarbamylase (mOTC) (NM 008769.3) or argininosuccinate synthetase (mASS) (NM 007494).

The various component sequences of the vectors constructed are identified below in Table 1 and the nucleotide sequences given in the Sequence Listing appearing at the end of the specification.

TABLE 1

Nucleotide sequences used in vector construction

| Name | Description | SEQ ID NO: |
|---|---|---|
| AAV2 ITR1 | AAV2-derived inverted terminal repeat 1. 181 bp | 1 |

TABLE 1-continued

Nucleotide sequences used in vector construction

| Name | Description | SEQ ID NO: |
|---|---|---|
| AAV2 ITR2 | AAV2-derived inverted terminal repeat 2. 181 bp | 2 |
| TRS I | PiggyBac transposon terminal repeat sequence I. 313 bp | 3 |
| TRS II | PiggyBac transposon terminal repeat sequence II. 230 bp | 4 |
| TRS I (short) | PiggyBac transposon terminal repeat sequence I-shortened (Meir et al., 2011, BMC Biotechnol 11:28). 67 bp | 5 |
| TRS II (short) | PiggyBac transposon terminal repeat sequence II-shortened (Meir et al., 2011, BMC Biotechnol 11:28). 40 bp | 6 |
| PiggyBac PBase | Coding region of PiggyBac transposase. 1785 bp | 7 |
| EGFP | Coding region of enhanced GFP. 720 bp | 8 |
| mOTC | Coding region of murine OTC gene. 1066 bp | 9 |
| mASS | Coding region of murine ASS gene. 1239 bp | 10 |
| hABCB4 var A | Coding region of codon optimised human ABCB4 transcript variant A. 3849 bp | 11 |
| hApoE enhancer | Human apolipoprotein E enhancer. 327 bp | 12 |
| hApoE-HCR enhancer | Human apolipoprotein E hepatic control region (derived from apolipoprotein E enhancer above). 192 bp | 13 |
| hAAT promoter | Human alpha-1 antitrypsin promoter. 397 bp | 14 |
| hAAT* promoter | Truncated human alpha-1 antitrypsin promoter. 254 bp | 15 |
| PRE | Woodchuck post-regulatory element. 589 bp | 16 |
| bGH polyA | Bovine growth hormone polyadenylation signal. 276 bp | 17 |
| SV40 polyA | Simian virus 40 polyadenylation signal. | 18 |
| Kozak | 134 bp Kozak sequence. 7 bp (CGCCACC) | — |

The vector constructs used in the present study comprised the above sequences constructed as follows:

piggyBac Transposase Vector (SEQ ID NO:19)
AAV2 ITR1
hApoE enhancer (two copies)
hAAT promoter
Kozak
piggyBac PBase
PRE
bGH polyA
AAV2 ITR2

EGFP Vector (SEQ ID NO:20)
AAV2 ITR1
TRS I
hApoE enhancer (two copies)
hAAT promoter
Kozak
EGFP
PRE
bGH polyA
TRS II
AAV2 ITR2

(A smaller version of this vector was also constructed using: the TRS I (short) and TRS II (short) sequences in place of TRS I and TRS II; a single copy of hApoE-HCR in place of two copies of hApoE enhancer; the hAAT* promoter in place of hAAT; and SV40 polyA in place of bGH polyA)

mOTC Vector (SEQ ID NO:21)
AAV2 ITR1
TRS I
hApoE enhancer (two copies)
hAAT promoter
Kozak
mOTC
PRE
bGH polyA
TRS II
AAV2 ITR2 mASS Vector (SEQ ID NO:22)
AAV2 ITR1
TRS I
hApoE enhancer (two copies)
hAAT promoter
Kozak
mASS
PRE
bGH polyA
TRS II
AAV2 ITR2 hABCB4 Vector (SEQ ID NO:23)
AAV2 ITR1
TRS I (short)
hApoE-HCR
hAAT* promoter
Kozak
hABCB4 varA (codon optimised)
PRE
SV40 polyA
TRS II (short)
AAV2 ITR2

Vector constructs were pseudoserotyped with liver-tropic vector capsids (AAV8 or AAVrh10), and viral particles were produced in human embryonic kidney (HEK) 293 cells by standard techniques. HEK293 cells were cultured in Dulbecco's modified Eagle medium (Gibco, Invitrogen, Grand Island, N.Y., USA) supplemented with 10% (v/v) fetal bovine serum (JRH Biosciences, Lenexa, Kans., USA) and 1% (w/v) L-glutamine (Gibco, Invitrogen) and maintained at 37° C. in a humidified 5% $CO_2$-air atmosphere. Vector genome titres were assigned by real-time quantitative PCR targeting the WPRE sequence as previously described (Cunningham et al., 2011, *Mol. Ther.* 19:854-859) or the EGFP transgene using the protocol as described for determining vector copy number (see below).

DNA was extracted from liver using standard phenol/chloroform and ethanol precipitation methods (Sambrook et al., 1989, *Molecular cloning: a laboratory manual.* Cold Spring Harbor Laboratory Press) Vector copy number of the transposon rAAVs was determined using the Quantitect Sybr Green Kit (Qiagen, Valencia, Calif., USA) and the following oligonucleotide sets targeting the relevant transgene: EGFP-F/EGFP-R, OTC-F/OTC-R and ASS-F/ASS-R. Vector copy number of the piggyBac transposase rAAV was determined using the Takara Sybr Premix Ex Taq Kit (Cat #RR420A) and oligonucleotides PB-F/PB-R. The PCR reactions were normalized using the Quantitect Sybr Green Kit (Qiagen, Valencia, Calif., USA) and oligonucleotide set GAPDH-F/GAPDH-R. Each reaction contained 100-150 ng of genomic DNA. Standards were prepared from linearized plasmid of the relevant vector, diluted in a background of 100-150 ng human genomic liver DNA per reaction (see Snyder et al., 1996, in Dracopoli et al. (eds.) *Protocols in Human Genetics.* John Wiley & Sons, Inc: Chichester, UK pp 12.0.1-12.1.24).

Example 2—Stable Expression of Hybrid AAV/Transposase Constructs in Mice

Figure 2:
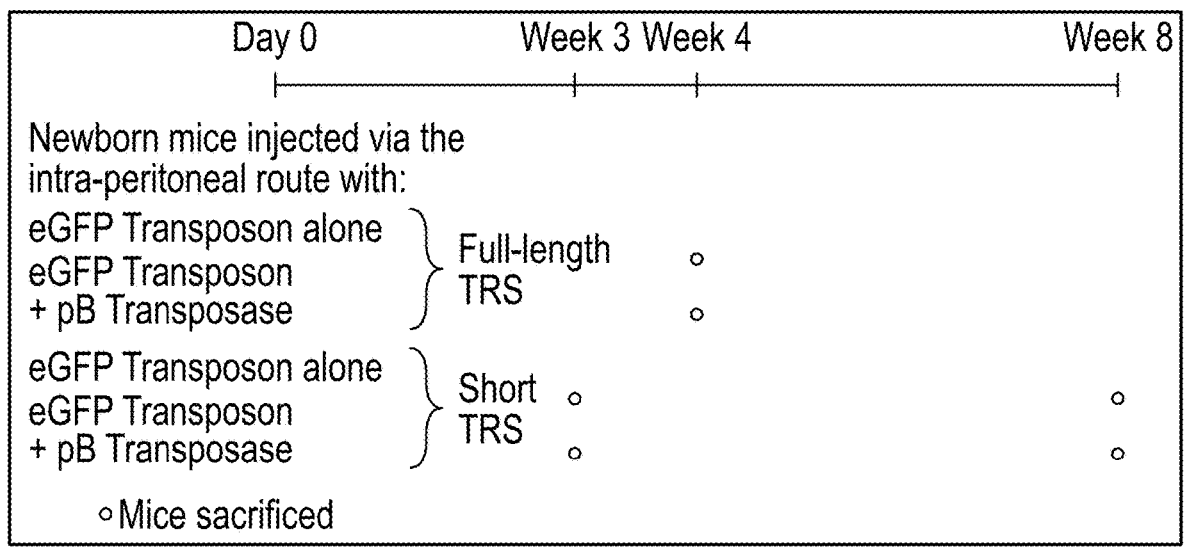
FIG. 2. Experimental design for testing transposon-donor transgene vectors encoding EGFP with either full length or short transposase recognition sites (TRS).

The ability of the AAV/transposase vector systems described in Example 1 to stably integrate and express a transgene in a host genome was determined using transposon-donor vectors encoding enhanced green fluorescent protein (EGFP) administered to C3H and FVB.129P2-Abcb4$^{tm1Bor}$ mice. Animals were housed in a temperature-controlled environment with 12-hour light/dark cycles with water and standard rodent chow (18.9% (wt/wt) protein; Specialty Feeds, Glen Forrest, Australia) supplied ad libitum. All experimental procedures were evaluated and approved by the institutional Animal Care and Ethics Committee. The experimental design is outlined in FIG. 2. Four mice were used for each group. Constructs were administered by injection via the intraperitoneal route in 20 µL volumes (diluted in PBS with calcium and magnesium) in newborn mice, at vector doses of $5 \times 10^{10}$ vg/mouse for the transposase vector, and $1 \times 10^{11}$-$5 \times 10^{11}$ vg/mouse for the transposon-transgene donor vector. Transposon-donor vectors encoding EGFP with either full length or short transposase recognition sites were co-administered with vector-encoded piggyBac transposase at days 0-1. Mice were sacrificed at week 3, 4 or 8, liver taken and EGFP expression observed via quantitative RT-PCR, immunofluorescence and fluorometry.

To measure mRNA expression, total RNA was extracted from 30-50 mg liver tissue using Trizol reagent (Life Technologies) according to the manufacturer's protocol and treated with DNAse I (Life Technologies). Reverse transcription using the SuperScript III First-Strand Synthesis SuperMix (Life Technologies) was used to generate cDNA. Quantitative RT-PCR was performed using the Quantitect Sybr Green Kit (Qiagen, Valencia, Calif., USA) and the relevant oligonucleotide sets.

For detection of EGFP protein, livers were removed and fixed in 4% (wt/v) paraformaldehyde (PFA) in phosphate-buffered saline (PBS), cryoprotected in 10-30% (wt/v) sucrose, and frozen in Optimum Cutting Temperature (OCT; TissueTek, Sakura Finetek USA, Torrance, Calif.) in iso-pentane/liquid Nitrogen for storage at −80° C. For co-localization of gene-modified cells with specific regions of liver architecture, the central veins were identified by immunohistochemical staining of glutamine synthetase. Frozen sections (5 µm) were permeabilized in methanol at −20° C. for 10 min, then reacted with a rabbit polyclonal anti-glutamine synthetase primary antibody (1/150 dilution; Abcam). Bound primary antibody was detected with an Alexa Fluor 594 donkey anti-rabbit secondary (1/1,000 dilution; Invitrogen, Carlsbad, Calif.). Sections were mounted in Immu-Mount (Thermo-Shandon) and imaged using an Olympus BX51 fluorescent microscope (Olympus, Centre Vally, Pa.). Direct EGFP fluorescence was detected using filters D480/30× (excitation) and D535/40m (emission), and Alexa Fluor 594 was detected using filters HQ560/55 (excitation) and HQ645/75 (emission). The percentage of transduced cells was determined by counting EGFP-positive cells in three random fields of view (10× magnification).

Figure 3A:
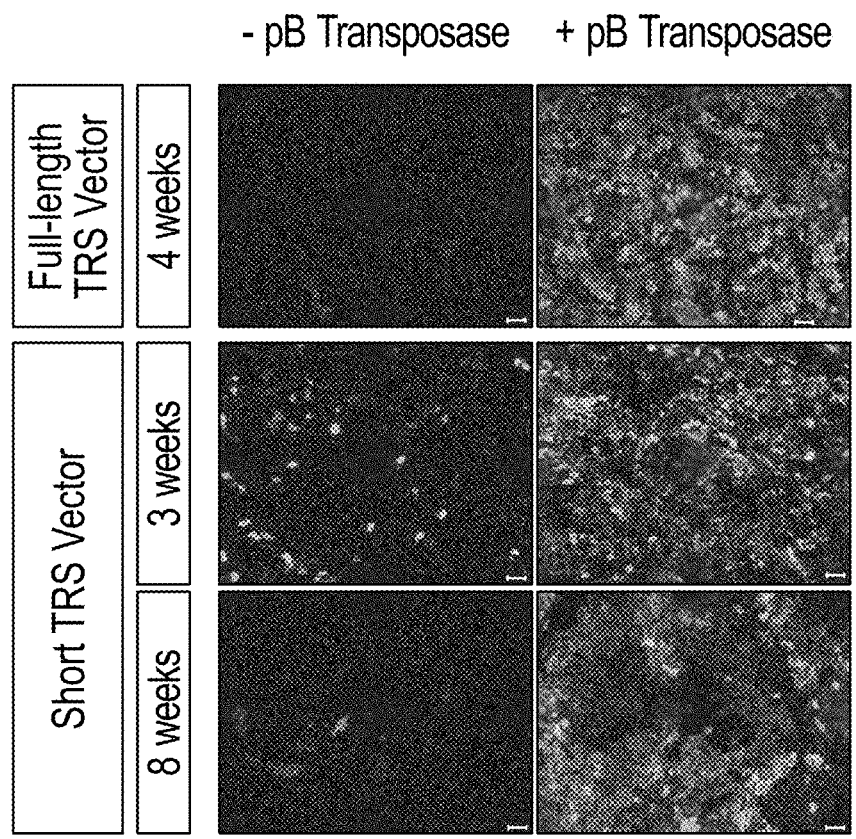
FIGS. 3A-3H.

FIG. 3A shows widespread and numerous EGFP-positive hepatocytes following concomitant delivery of rAAV-encoded piggyBac transposase and transposon-transgene donor vectors compared with EGFP transposon vector alone. There was a >20-fold increase in the number of stably gene-modified hepatocytes from 2.4% to 50%, when the transposase expression vector was co-transfected with the EGFP transposon-containing vector (FIG. 3A).

Figure 3B:
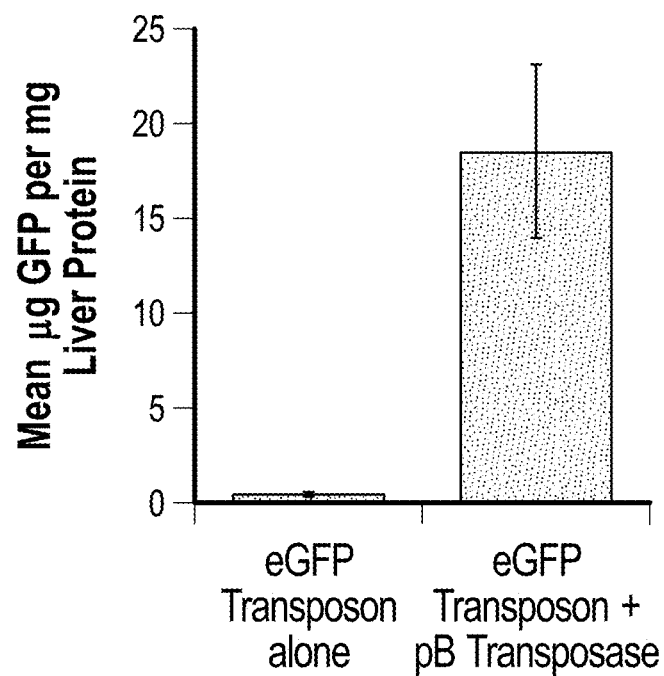

Fluorometric analysis of liver lysates comprised homogenization of 50 mg liver in 750 uL Lysis Buffer: 0.5% Triton X-100, 0.01M Hepes, protease inhibitors; incubated 1 hr on ice then centrifuged at 14000 rpm for 20 min, 4° C. The total protein content of the lysate was measured (DC Protein assay; Bio-Rad, Hercules, Calif.) and individual samples adjusted to a final concentration of 0.5 mg/mL. A standard curve was prepared using recombinant EGFP protein (BioVision Research Products, Mountain View, Calif.). Equal volumes of samples and standards were loaded into black plastic 96-well plates (PerkinElmer, Boston, Mass.) and EGFP fluorescence quantitated on a VICTOR3 multilabel reader (PerkinElmer) using an excitation and emission filter set at 485 nm/535 nm. Fluorometry confirmed the observed higher levels of EGFP expression in EGFP transposon+ transposase livers (FIG. 3B).

Figure 3C:
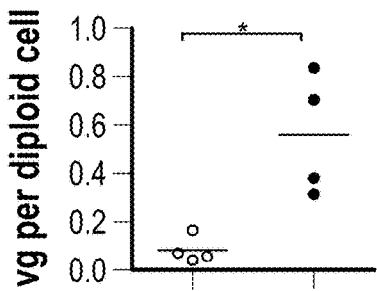
Figure 3D:
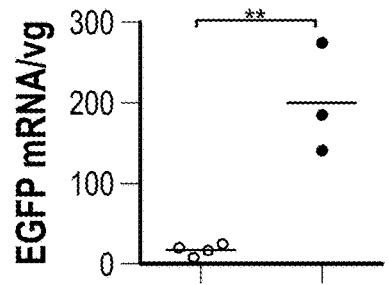
Figure 3E:
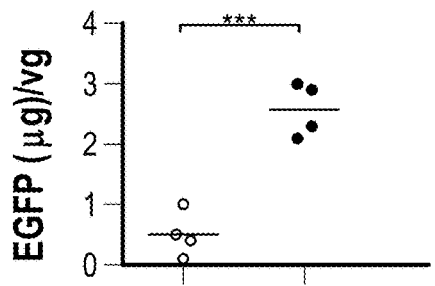
Figure 3F:
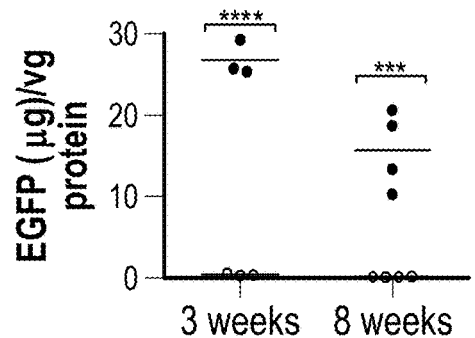
Figure 3G:
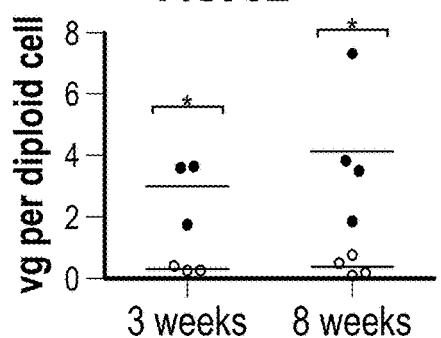
Figure 3H:
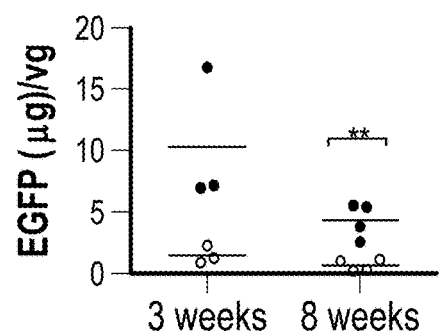

Interestingly, the increase in the number of stably gene-modified hepatocytes correlated with a 43-fold higher level of EGFP protein expression in liver lysates (FIG. 3B), and a relatively lower, but nevertheless impressive, 7-fold increase in vector genome copy number per diploid cell (FIG. 3C). This indicates significantly higher levels of EGFP mRNA (FIG. 3D) and protein (FIG. 3E) expression from transposed expression cassettes than from those stably maintained (presumably through integration) in the host cell as part of an AAV provirus.

The system was also tested using minimal piggyBac TIRs to increase the cargo capacity of the vector-encoded transposable element (FIG. 1B). Quantitatively and qualitatively equivalent data were obtained (FIG. 3A bottom panels and FIGS. 3F-H). The hybrid system performed similarly in male and female mice, delivering an impressive 70-fold and 103-fold increase in stable EGFP expression at 3 and 8 weeks of age, respectively, over the transposon vector delivered alone. The peri-venous and peri-portal zones of the hepatic lobule, which exhibit metabolic zonation, were targeted with equivalent efficiency.

Example 3—Gene Therapy in a Mouse Model of OTC Deficiency

Figure 4:
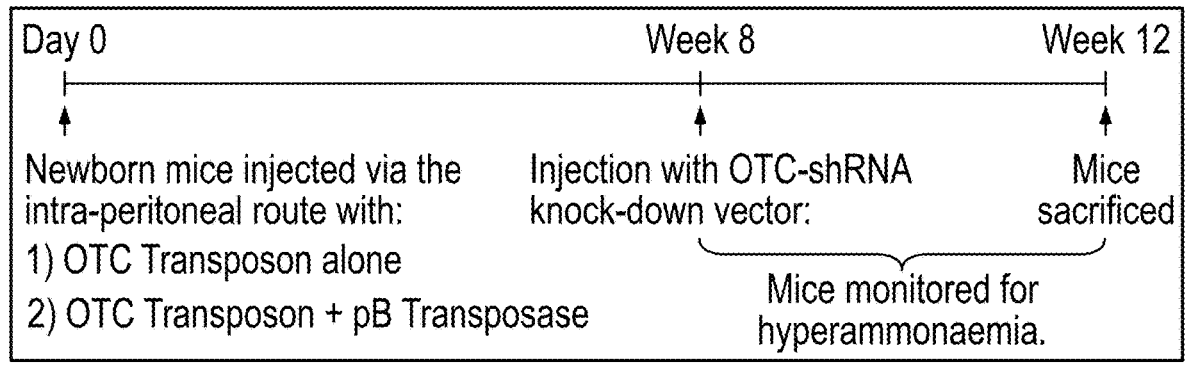
FIG. 4. Experimental design for testing phenotype correction following co-delivery of the OTC-encoding transposon-transgene vector and the piggyBac transposase vector, in the spf$^{ash}$ mouse model of OTC deficiency.

The hybrid AAV/transposase constructs described in Example 1 were used to demonstrate phenotype correction in a mouse model of OTC deficiency (the spf$^{ash}$ mouse model). Mice used were strain B6EiC3Sn a/A-Otc$^{spf-ash}$/J (provided by The Jackson Laboratory). The disease phenotype presents early in life in neonates or juveniles. As such, vector treatment was delivered to mice during the neonatal period. Constructs were administered by injection via the intraperitoneal route in 20 µL volumes (diluted in PBS with calcium and magnesium) in newborn mice (1-2 days), at vector doses of $5 \times 10^{10}$ vg/mouse for the transposase vector, and $1 \times 10^{11}$ vg/mouse for the transposon-transgene donor vector. The experimental design is outlined in FIG. 4 with 12 mice receiving OTC-transposon-encoding AAV2/8 vector alone, and 12 mice receiving OTC transposon-encoding vector in combination with the piggyBac transposase-encoding AAV2/8 vector.

Figure 5A:
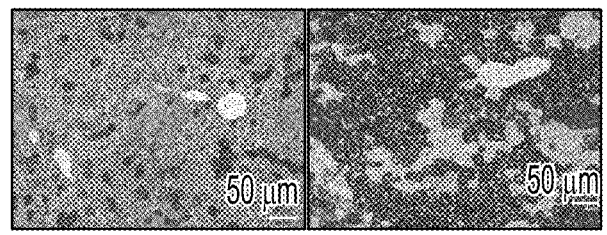
FIGS. 5A-5F.
Figure 5B:
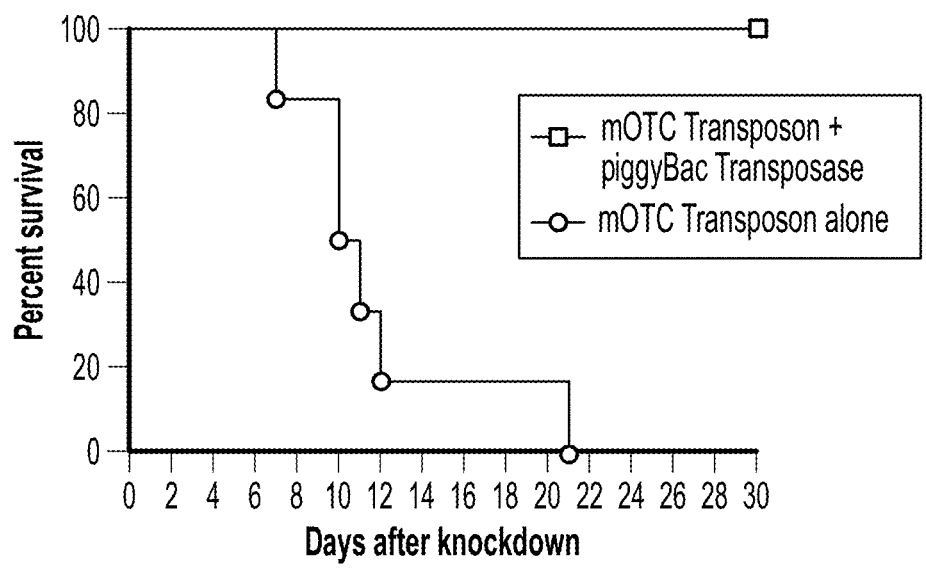
Figure 5C:
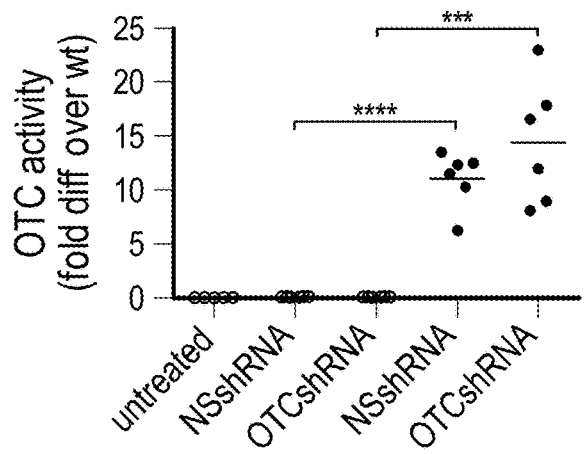
Figure 5D:
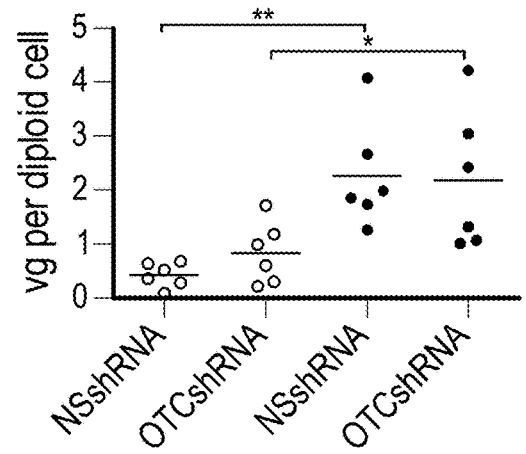
Figure 5E:
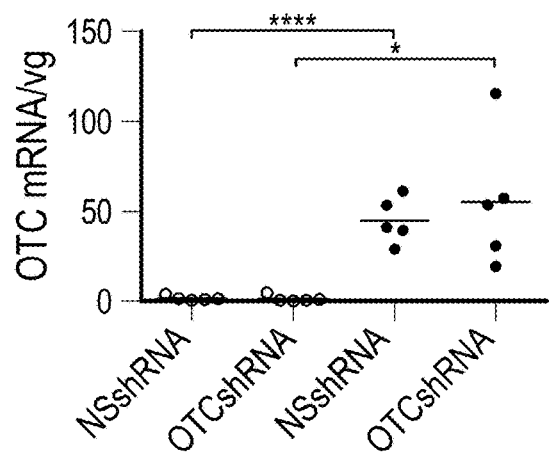
Figure 5F:
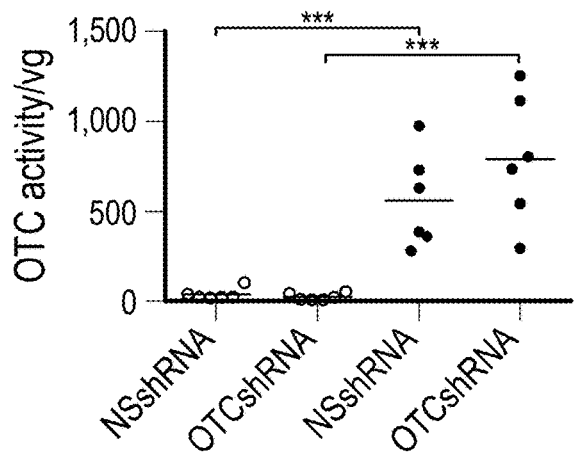

Liver sections from mice sacrificed at week 12 were analysed for OTC activity according to the method described in Ye et al., 1996, J Biol Chem 271:3639-3646. Liver sections showed widespread OTC activity in mice that had been administered both the OTC-encoding transposon-transgene vector and the piggyBac transposase vector (FIG. 5A, right panel), compared with mice that received OTC-encoding transposon-transgene vector alone (FIG. 5A, left panel). Mice treated in the newborn period with the rAAV OTC transposon alone (n=6 mice) developed severe hyperammonaemia, necessitating euthanasia, when background endogenous OTC activity was knocked down in early adulthood, while mice treated with both the OTC-expressing transposon and piggyBac transposase-encoding vectors (n=6 mice) survived, as did all cohorts injected with a rAAV expressing a non-specific (NS) shRNA (data not shown). Kaplan-Meier survival analysis using Prism (GraphPad software) was conducted of mice receiving the OTC-encoding transposon-transgene vector alone or in combination with piggyBac transposase vector, followed by knockdown of residual endogenous OTC activity at adulthood (FIG. 5B). Survival curves show, for each plotted time on the X axis, the portion of all individuals surviving as of that time. Survival correlated with the approximately 66-fold increase in the proportion of visibly OTC-positive hepatocytes in liver sections (FIG. 5A) and a 126-fold increase in OTC activity to massively supra-physiological levels (FIG. 5C). Consistent with data generated using the EGFP-encoding constructs, the increase in stably maintained vector genome copies was less dramatic (FIG. 5D), again indicating higher levels of transgene expression from transposed expression cassettes (FIGS. 5E and 5F).

For ammonia analysis, blood was collected by cardiac puncture into lithium heparin coated tubes and immediately centrifuged at 7,500×g for 5 minutes at 4° C. The plasma was frozen in liquid Nitrogen, and stored at −80° C. Ammonia was measured using the Ammonia Assay Kit (Sigma-Aldrich, St Louis, Mo.). All mice that received both the OTC-encoding transposon-transgene vector and the piggyBac transposase vector survived to the experimental endpoint (28 days), with plasma ammonia in the normal range (79.7±10.1 µM) while all mice receiving OTC-encoding transposon-transgene vector alone became unwell with elevated blood ammonia (954.3±173.3 µM) within 21 days of knockdown.

Example 4—Gene Therapy in Mouse Model of ASS Deficiency

The hybrid AAV/transposase constructs described in Example 1 were used to demonstrate phenotype correction in a neonatal lethal knock-out mouse model of ASS deficiency (the citrullinaemic mouse model). Mice used were strain B6;129S7-Ass1$^{tm1Bay}$/J (provided by The Jackson Laboratory). The disease phenotype presents early in life in neonates or juveniles. As such, vector treatment was delivered to mice during the perinatal period. Pregnant females were anesthetised using isoflurane inhalation anaesthesia. Buprenorphine (0.01 mg/kg) (Reckitt Benckiser, West Ryde, Australia) was given by subcutaneous injection as an analgesic. A laparotomy was performed to expose the uterus and constructs were administered to each foetus by injection via the intraperitoneal route in 5 µL volumes (diluted in PBS with calcium and magnesium) at embryonic day 15, at vector doses of 5×10$^{10}$ vg/mouse for the transposase vector, and 1×10$^{11}$ vg/mouse for the transposon-transgene donor vector. The abdominal incision was then closed with sutures. A subcutaneous injection of ampicillin was given and mice were maintained on carprofen (0.14 mL/250 mL) given orally in drinking water for 7 days. Pups were born around E20, designated Day 0. From birth, pups were given a daily intra-peritoneal injection of L-arginine (1 g/kg) until adulthood, after which injections were reduced to 3 times weekly. Mice were monitored and sacrificed from 3 to 6 months of age. The experimental design is outlined in FIG. 6.

To determine the ability of the ASS-encoding transposon-transgene vector to correct the deficient phenotype in the mice, ammonia and orotic acid levels were analysed. For ammonia analysis, blood was collected into lithium heparin coated tubes by cardiac puncture and immediately centrifuged at 7,500×g for 5 minutes at 4° C. The plasma was frozen in liquid Nitrogen and stored at −80° C. Ammonia was measured using the Ammonia Assay Kit (Sigma-Aldrich, St Louis, Mo.). For orotic acid analysis, urine was collected over a 24 hour period on Whatman filter paper, eluted, and analyzed for orotic acid levels using Liquid Chromatography/Tandem Mass Spectrometry. Results were standardized against creatinine levels measured by the modified Jaffe reaction.

Phenotype correction in the ASS-deficient citrullinaemic mouse model was successful, with treated mice surviving to adulthood. Following a single prenatal dose, mutant mice not only survived the neonatal period, but remained healthy into adulthood, with one cohort maintained to 6 months of age. Adult treated mutant males and females were fertile and females carried pups to full-term. A sparse fur, abnormal skin and hair phenotype was evident from birth reminiscent of that observed in OTC-deficient Spf$^{ash}$ mice, which improved from weaning age (FIGS. 7A and 7B). Orotic acid analysis showed that while normalisation of urinary orotic acid was variable among treated mice (n=15) (FIG. 7C), treated mice were protected against hyperammonaemia (Table 2).

Figure 7D:
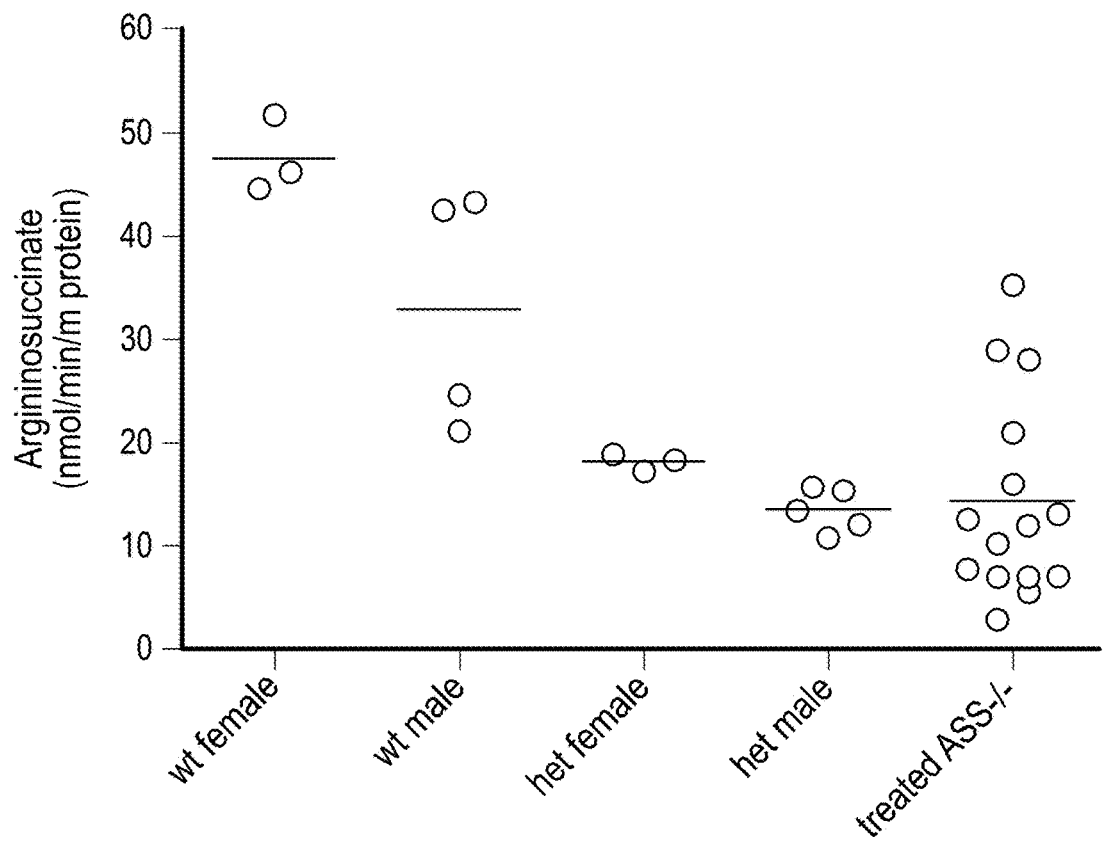

ASS activity in the liver was determined using a method based on the conversion of $^{14}$C-aspartate to $^{14}$C-argininosuccinate (Kok et al., 2013, Mol. Ther. 21:1823-1831) All mice exhibited robust control of hyperammonaemia despite inter-mouse variability in AAS activity (FIG. 7D). Blood plasma from treated mice was analysed for the amino acids arginine, citrulline and ornithine. Quantitation plasma was deproteinized by ultrafiltration before addition of an internal standard, then analyzed by ion-exchange chromatography with postcolumn ninhydrin detection on a Biochrom 30 amino acid analyzer (Biochrom, Cambridge, UK). Table 2 shows that citrulline, arginine and ornithine were not normalised compared to wildtype controls, despite ammonia being maintained in the normal range.

TABLE 2

Biochemical analyses of plasma from treated ASS-deficient mice.

|  | Treated mice | WT control mice |
| --- | --- | --- |
| Citrulline (µmol/L) | 721 ± 103 | 78 ± 7.2 |
| Arginine (µmol/L) | 88 ± 19.6 | 138 ± 17.7 |
| Ammonia (µmol/L) | 71 ± 11.1 | 48 ± 6.7 |
| Ornithine (µmol/L) | 43 ± 4.29 | 66 ± 8.1 |

ASS protein expression and localization in treated mice was investigated by immunohistochemistry. Formalin-fixed liver sections were dewaxed and rehydrated in xylene and an ethanol gradient. Antigen retrieval was performed using 10 mmol/l sodium citrate buffer pH 7.4, followed by blocking with 0.3% (v/v) hydrogen peroxidize for 30 minutes. Endogenous avidin and biotin were blocked using the avidin-biotin kit (Vector Laboratories, Burlingame, Calif.), following the manufacturer's instructions. Sections were then blocked with 10% (v/v) donkey serum and stained with a goat antibody against mouse ASS (2.5 µg/ml, ab77590; Abcam, Cambridge, UK) overnight at 4° C. After washing in phosphate-buffered saline with 0.05% Tween-20, samples were incubated with a biotinylated donkey anti-goat secondary antibody (1.2 µg/ml, 705-065-147; Jackson ImmunoResearch, West Grove, Pa.) and detected with horseradish peroxidase, using the Vectastain Elite ABC (PK-7100, Vector Laboratories) and 3,3'-Diaminobenzidine liquid substrate (D6190, Sigma-Aldrich) as per manufacturer's instructions.

To identify central veins, detection of glutamine synthetase was carried out using a rabbit polyclonal anti-glutamine synthetase primary antibody (1/150 dilution, ab16802; Abcam). Bound primary antibody was detected with a biotinylated donkey anti-rabbit secondary antibody (1/1000, 711-065-152, Jackson ImmunoResearch) and the Vectastain Elite ABC system (PK-7100, Vector Laboratories), followed by application of VIP substrate (Vector Laboratories) as per the manufacturer's instructions. Following completion of ASS and glutamine synthetase detection, sections were counterstained with hematoxylin, and mounted using Ultramount No. 4 (Fronine) Images were captured using a Zeiss Axio Imager.A1 microscope and Spot Imaging software.

Figure 7E:
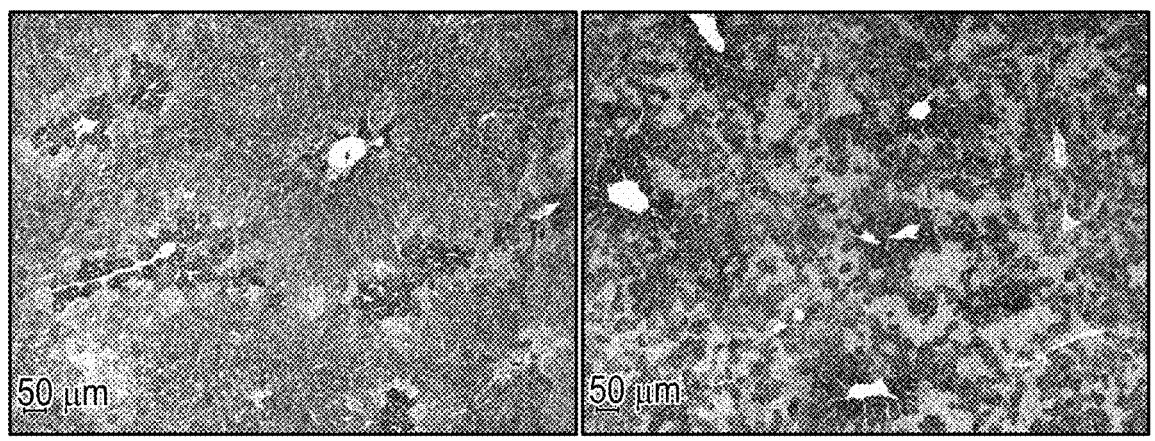

As shown in FIG. 7E, ASS protein was localised in the liver of treated mice, co-localising with glutamine synthetase. The typical gradient of expression of endogenous ASS activity is shown in a wildtype untreated mouse (FIG. 7E, left panel), while widespread high levels of vector-encoded ASS protein can be seen in a mutant vector-treated mouse (FIG. 7E, right panel).

Example 5—Gene Therapy in Mouse Model of Progressive Intrahepatic Cholestasis

Progressive Familial Intrahepatic Cholestasis Type 3 (PFIC3) is a hereditary chronic liver disease with predominantly childhood onset. Affected individuals, carrying 2 mutated copies of the ABCB4 gene, have abnormal liver bile production with absent biliary phosphatidylcholine. Approximately 50% of all patients require liver transplantation at an average age of 7.5 years. (Jacquemin, 2012, *Clinics and Research in Hepatology and Gastroenterology* 36 Suppl 1:S26-35). The Abcb4-knockout mouse model shows progressive liver pathology with early onset, which recapitulates the PFIC3 liver disease phenotype.

The inventors used this mouse model to demonstrate correction of the liver disease phenotype using the hybrid rAAV-piggyBac transposon system (FVB.129P2-Abcb4$^{tm1Bor}$/J, provided by The Jackson Laboratory). The disease phenotype presents early in life in neonates or juveniles. As such, vector treatment was delivered to mice during the neonatal period. Constructs were administered by injection via the intraperitoneal route in 20 uL volumes (diluted in PBS with calcium and magnesium) in newborn mice, at vector doses of $5\times10^{10}$ vg/mouse for the transposase vector, and $5\times10^{11}$ vg/mouse for the transposon-transgene donor vector. The experimental design is outlined in FIG. 8.

The piggyBac transposon developed for these sets of experiments encoded a codon-optimised human ABCB4 sequence (SEQ ID NO:11) with short transposon recognition sites (SEQ ID NO:5 and SEQ ID NO:6) flanking the expression cassette, inside the AAV2 inverted terminal repeat sequences (SEQ ID NO:1 and SEQ ID NO:2).

A commercial colormetric assay was used to quantify biliary phosphatidylcholine (EnzyChrom™ Phospholipid Assay Kit, BioAssay Systems). To obtain bile for this analysis, bile was aspirated directly from the gallbladder in mice that had been fasted for at least 4 hours, performed as part of the termination procedure. Histology was performed on 4 μm liver sections that were formalin-fixed and embedded in paraffin. H+E and Sirius red stains were performed by the Histology Unit at Westmead Millennium Institute.

As shown in FIG. 9, mice that received a single therapeutic injection of the hABCB4-encoding transposon-transgene donor vector co-administered with the piggyBac transposase vector, had significantly raised phosphatidylcholine concentrations in bile and absence of liver pathology, compared with untreated control homozygotes.

The invention claimed is:

1. A method for treating a disease of, affecting, or associated with, proliferating liver cells, comprising administering to a subject in need thereof (i) a recombinant AAV (rAAV) vector comprising a transgene operably linked to a liver-specific promoter and flanked by piggyBac transposon-derived inverted terminal repeat sequences, which sequences are in turn flanked by AAV-derived inverted terminal repeat regions; and (ii) a vector encoding a piggyBac transposase and providing transient expression of the transposase, wherein the transposase recognises said piggyBac transposon-derived inverted terminal repeat sequences and directs the genomic integration of the transgene into the genome of the proliferating liver cells, wherein said administration results in the stable integration and expression of the transgene in the proliferating liver cells to thereby treat the disease, and wherein the disease is associated with the deficiency of one or more gene products in the proliferating liver cells, and wherein expression of the transgene normalizes production and activity of the deficient Rene product.

2. A method according to claim 1, wherein the disease is a paediatric liver disease.

3. A method according to claim 2, wherein the paediatric liver disease is selected from OTC deficiency, ASS deficiency and progressive familial intrahepatic cholestasis.

4. A method according to claim 3, wherein the progressive familial intrahepatic cholestasis is progressive familial intrahepatic cholestasis type 3.

5. A method according to claim 3, wherein the disease is OTC deficiency and the transgene comprises a polynucleotide encoding ornithine transcarbamylase (OTC).

6. A method according to claim 3, wherein the disease is ASS deficiency and the transgene comprises a polynucleotide encoding argininosuccinate synthetase (ASS).

7. A method according to claim 3, wherein the disease is progressive familial intrahepatic cholestasis and the transgene comprises a polynucleotide encoding ATP-binding cassette subfamily B member 4 (ABCB4).

8. A method according to claim 1, wherein the transposase is provided in a form so as to allow transient expression of the transposase in the proliferating liver cells.

9. A method according to claim 1, wherein the transposase is administered to the subject via a second rAAV vector comprising a polynucleotide encoding the transposase, optionally flanked by AAV-derived inverted terminal repeat regions.

* * * * *

SEQUENCE LISTING

<160> NUMBER OF SEQ ID NOS: 23

<210> SEQ ID NO 1
<211> LENGTH: 181
<212> TYPE: DNA
<213> ORGANISM: adeno-associated virus 2

<400> SEQUENCE: 1

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
a                                                                     181
```

<210> SEQ ID NO 2
<211> LENGTH: 181
<212> TYPE: DNA
<213> ORGANISM: adeno-associated virus 2

<400> SEQUENCE: 2

```
tagagcatgg ctacgtagat aagtagcatg gcgggttaat cattaactac aaggaacccc      60
tagtgatgga gttggccact ccctctctgc gcgctcgctc gctcactgag gccgggcgac     120
caaaggtcgc ccgacgcccg gctttgccc gggcggcctc agtgagcgag cgagcgcgca     180
g                                                                     181
```

<210> SEQ ID NO 3
<211> LENGTH: 313
<212> TYPE: DNA
<213> ORGANISM: Artificial
<220> FEATURE:
<223> OTHER INFORMATION: piggyBac transposon

<400> SEQUENCE: 3

```
ttaaccctag aaagatagtc tgcgtaaaat tgacgcatgc attcttgaaa tattgctctc    60
tctttctaaa tagcgcgaat ccgtcgctgt gcatttagga catctcagtc gccgcttgga   120
gctcccgtga ggcgtgcttg tcaatgcggt aagtgtcact gattttgaac tataacgacc   180
gcgtgagtca aaatgacgca tgattatctt ttacgtgact tttaagattt aactcatacg   240
ataattatat tgttatttca tgttctactt acgtgataac ttattatata tatattttct   300
tgttatagat atc                                                     313
```

<210> SEQ ID NO 4
<211> LENGTH: 230
<212> TYPE: DNA
<213> ORGANISM: Artificial
<220> FEATURE:
<223> OTHER INFORMATION: piggyBac transposon

<400> SEQUENCE: 4

```
tttgttactt tatagaagaa attttgagtt tttgtttttt tttaataaat aaataaacat    60
aaataaattg tttgttgaat ttattattag tatgtaagtg taaatataat aaaacttaat   120
atctattcaa attaataaat aaacctcgat atacagaccg ataaaacaca tgcgtcaatt   180
ttacgcatga ttatctttaa cgtacgtcac aatatgatta tctttctagg             230
```

<210> SEQ ID NO 5
<211> LENGTH: 67
<212> TYPE: DNA
<213> ORGANISM: Artificial
<220> FEATURE:
<223> OTHER INFORMATION: piggyBac transposon

<400> SEQUENCE: 5

```
ttaaccctag aaagataatc atattgtgac gtacgttaaa gataatcatg cgtaaaattg    60
acgcatg                                                             67
```

<210> SEQ ID NO 6
<211> LENGTH: 40
<212> TYPE: DNA
<213> ORGANISM: Artificial
<220> FEATURE:
<223> OTHER INFORMATION: piggyBac transposon

<400> SEQUENCE: 6

```
gcatgcgtca attttacgca gactatcttt ctagggttaa                          40
```

<210> SEQ ID NO 7
<211> LENGTH: 1785
<212> TYPE: DNA
<213> ORGANISM: Artificial
<220> FEATURE:
<223> OTHER INFORMATION: piggyBac transposon

<400> SEQUENCE: 7

```
atgggtagtt ctttagacga tgagcatatc ctctctgctc ttctgcaaag cgatgacgag    60
cttgttggtg aggattctga cagtgaaata tcagatcacg taagtgaaga tgacgtccag   120
```

| | |
|---|---|
| agcgatacag aagaagcgtt tatagatgag gtacatgaag tgcagccaac gtcaagcggt | 180 |
| agtgaaatat tagacgaaca aaatgttatt gaacaaccag gttcttcatt ggcttctaac | 240 |
| agaatcttga ccttgccaca gaggactatt agaggtaaga ataaacattg ttggtcaact | 300 |
| tcaaagtcca cgaggcgtag ccgagtctct gcactgaaca ttgtcagatc tcaaagaggt | 360 |
| ccgacgcgta tgtgccgcaa tatatatgac ccacttttat gcttcaaact atttttact | 420 |
| gatgagataa tttcggaaat tgtaaaatgg acaaatgctg agatatcatt gaacgtcgg | 480 |
| gaatctatga caggtgctac atttcgtgac acgaatgaag atgaaatcta tgctttcttt | 540 |
| ggtattctgg taatgacagc agtgagaaaa gataaccaca tgtccacaga tgacctcttt | 600 |
| gatcgatctt tgtcaatggt gtacgtctct gtaatgagtc gtgatcgttt tgattttttg | 660 |
| atacgatgtc ttagaatgga tgacaaaagt atacggccca cacttcgaga aaacgatgta | 720 |
| tttactcctg ttagaaaaat atgggatctc tttatccatc agtgcataca aaattacact | 780 |
| ccagggctc atttgaccat agatgaacag ttacttggtt ttagaggacg gtgtccgttt | 840 |
| aggatgtata tcccaaacaa gccaagtaag tatggaataa aaatcctcat gatgtgtgac | 900 |
| agtggtacga agtatatgat aaatggaatg ccttatttgg gaagaggaac acagaccaac | 960 |
| ggagtaccac tcggtgaata ctacgtgaag gagttatcaa agcctgtgca cggtagttgt | 1020 |
| cgtaatatta cgtgtgacaa ttggttcacc tcaatccctt tggcaaaaaa cttactacaa | 1080 |
| gaaccgtata agttaaccat tgtgggaacc gtgcgatcaa acaaacgcga gataccggaa | 1140 |
| gtactgaaaa acagtcgctc caggccagtg ggaacatcga tgttttgttt tgacggaccc | 1200 |
| cttactctcg tctcatataa accgaagcca gctaagatgg tatacttatt atcatcttgt | 1260 |
| gatgaggatg cttctatcaa cgaaagtacc ggtaaaccgc aaatggttat gtattataat | 1320 |
| caaactaaag gcggagtgga cacgctagac caaatgtgtt ctgtgatgac ctgcagtagg | 1380 |
| aagacgaata ggtggcctat ggcattattg tacggaatga taaacattgc ctgcataaat | 1440 |
| tcttttatta tatacagcca taatgtcagt agcaagggag aaaaggttca agtcgcaaa | 1500 |
| aaatttatga gaaaccttta catgagcctg acgtcatcgt ttatgcgtaa gcgtttagaa | 1560 |
| gctcctactt tgaagagata tttgcgcgat aatatctcta atattttgcc aaatgaagtg | 1620 |
| cctggtacat cagatgacag tactgaagag ccagtaatga aaaacgtac ttactgtact | 1680 |
| tactgccct ctaaaataag gcgaaaggca atgcatcgt gcaaaaaatg caaaaaagtt | 1740 |
| atttgtcgag agcataatat tgatatgtgc caaagttgtt tctga | 1785 |

<210> SEQ ID NO 8
<211> LENGTH: 720
<212> TYPE: DNA
<213> ORGANISM: Artificial
<220> FEATURE:
<223> OTHER INFORMATION: Synthetic sequence

<400> SEQUENCE: 8

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |

```
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 9
<211> LENGTH: 1066
<212> TYPE: DNA
<213> ORGANISM: Mus musculus
<220> FEATURE:
<221> NAME/KEY: misc_feature
<222> LOCATION: (256)..(256)
<223> OTHER INFORMATION: n is a, c, g, or t

<400> SEQUENCE: 9

```
atgctgtcta atttgaggat cctgctcaac aatgcagctc ttagaaaggg tcacacttct     60
gtggttcgac attttggtg tgggaagcca gtccaaagtc aagtacagct gaaaggccgt    120
gacctcctca ccttgaagaa cttcacagga gaggagattc agtacatgct atggctctct    180
gcagatctga aattcaggat caagcagaaa ggagaatatt tacctttatt gcaagggaaa    240
tccttaggaa tgattntttg agaaaagaag tactcgaaca agactgtcca cagaaacagg    300
ctttgctctg ctgggaggac acccttcctt tcttaccaca caagacattc acttgggtgt    360
gaatgaaagt ctcacagaca ccgctcgtgt cttatctagc atgacagatg cagtgttagc    420
tcgagtgtat aaacaatcag atctggacac cctggctaaa gaagcatcca tcccaattgt    480
caatggactg tcagacttgt atcatcctat ccagatcctg gctgattacc ttacactcca    540
ggaacactat ggctctctca aggtcttac cctcagctgg atagggatg gaacaatat     600 cttgcactct atcatgatga gtgctgcaaa attcggatg caccttcaag cagctactcc    660
aaagggttat gagccagatc ctaatatagt caagctagca gagcagtatg ccaaggagaa    720
tggtaccaag ttgtcaatga caaatgatcc actggaagca gcacgtggag gcaatgtatt    780
aattacagat acttggataa gcatgggaca agaggatgag aagaaaaagc gtcttcaagc    840
tttccaaggt taccaggtta cgatgaagac tgccaaagtg gctgcgtctg actggacatt    900
tttacactgt ttgcctagaa agccagaaga agtggatgat gaagtatttt attctccacg    960
gtcattagtg ttcccagagg cagagaatag aaagtggaca atcatggctg tcatggtatc    1020
cctgctgaca gactactcac ctgtgctcca gaagccaaag ttttga                   1066
```

<210> SEQ ID NO 10
<211> LENGTH: 1239
<212> TYPE: DNA
<213> ORGANISM: Mus musculus

<400> SEQUENCE: 10

```
atgtccagca agggctctgt ggttctggcc tacagtggtg gcctggacac ctcctgcatc     60
ctcgtgtggc tgaaggaaca aggctatgat gtcatcgcct acctggccaa cattggccag    120
aaggaagact ttgaggaagc caggaagaag gcgctgaagc ttggggccaa aaaggtgttc    180
attgaggatg tgagcaagga atttgtggaa gagttcatct ggcctgctgt ccagtccagt    240
gcactctacg aggaccgcta tctcctgggc acctctctcg ccaggccttg catagctcgc    300
agacaggtgg agattgccca gcgtgaaggg gccaagtatg tgtctcacgg cgccacggga    360
```

```
aaggggaatg accaggtccg ctttgagctc acctgctatt cactggcacc ccagattaag      420
gtcatcgctc cctggaggat gcctgagttt tacaaccggt tcaagggccg aaatgatctg      480
atggagtatg caaagcaaca cggaatcccc atccctgtca cccccaagag cccctggagt      540
atggatgaaa acctcatgca catcagctat gaggctggga tcctggaaaa ccccaagaat      600
caagcacctc cgggtctcta cacaaaaact caggaccctg ccaaagcacc aacagccca      660 gatgtccttg agatagaatt caaaaaaggg gtccctgtga aggtgaccaa catcaaagat      720
ggcacaaccc gcaccacatc cctggaactc ttcatgtacc tgaacgaagt tgcgggcaag      780
cacggagtgg gtcgcattga catcgtggag aaccgcttca ttggaatgaa gtcccgaggt      840
atctacgaga ccccagcagg gaccatcctt taccacgctc atttagacat agaggccttc      900
acgatggatc gggaagtacg caaaatcaag cagggcctgg gcctcaaatt cgcagagctc      960
gtatacacag gtttctggca cagccctgaa tgtgaatttg ttcgccactg tatccagaag     1020
tcccaggagc gggtagaagg gaaggtgcag gtgtctgtct tcaagggcca agtgtacatc     1080
ctcggtcggg agtctccact ttcactctac aatgaagagc tggtgagcat gaacgtgcag     1140
ggcgactatg agcccatcga cgccactggc ttcatcaata tcaactcgct caggctgaag     1200
gagtaccatc gccttcagag caaggtcact gccaaatag                            1239
```

<210> SEQ ID NO 11
<211> LENGTH: 3849
<212> TYPE: DNA
<213> ORGANISM: Homo sapiens

<400> SEQUENCE: 11

```
gccgccacca tggacctgga ggcagcaaag aatggaaccg catggagacc aacatcagca       60
gagggggact tcgaactggg tatttcaagc aagcagaagc gcaagaaaac taagaccgtg      120
aaaatgatcg gggtcctcac cctgttccga tactccgact ggcaggataa gctctttatg      180
tctctgggca caatcatggc cattgctcac gggtctggtc tccctctgat gatgatcgtg      240
ttcggggaga tgaccgacaa atttgtcgat acagccggta atttcagctt tccagtgaac      300
ttctctctca gtctgctcaa ccccggcaag atcctggagg aagagatgac tcgctatgca      360
tactattact ctggactggg agctggggtg ctggtcgcag cttacatcca ggtgagtttc      420
tggaccctgg cagctggacg gcagatccgc aaaattcgac agaagttctt tcatgccatc      480
ctgagacagg agattgggtg gtttgacatc aatgatacca cagaactcaa caccggctg      540 acagacgaca tcagcaaaat ttccgagggt atcggcgata agtgggaat gttctttcag      600 gcagtcgcca ctttctttgc cggattcatt gtcgggttta tccgggggttg gaagctgacc      660 ctggtcatca tggctatttc accaatcctc gggctgagcg ccgcagtgtg ggcaaagatc      720
ctctctgcct tcagtgacaa agagctggcc gcttatgcta aggcaggagc tgtggctgaa      780
gaggcactgg gagcaattcg aaccgtgatc gcctttggcg gacagaataa ggaactcgag      840
aggtaccaga aacacctgga gaacgctaag gaaatcggga ttaagaaagc tatttccgca      900
aacatctcta tgggtattgc tttcctgctc atctatgcat cttacgcact cgccttttgg      960
tatggcagca ccctggtcat cagcaaggag tacactatcg aaatgcaat gaccgtcttc     1020 ttttctatcc tgattggggc tttcagtgtg ggtcaggcag cccctgcat cgacgctttc     1080 gcaaatgcac gcggcgctgc atacgtgatc ttcgacatca ttgataacaa ccctaagatc     1140
gactcattca gcgagagggg gcacaaacca gatagcatta agggtaatct ggaattcaac     1200
```

```
gacgtgcatt tttcataccc tagcagagcc aatgtcaaga tcctgaaagg actcaacctg    1260
aaagtgcaga gcgggcagac tgtggctctg gtcggtagct ccggatgcgg gaagtccact    1320
accgtgcagc tcattcagcg gctgtatgac ccagatgagg gcacaatcaa cattgacgga    1380
caggacatcc gcaacttcaa tgtcaactac ctgcgagaga tcattggcgt ggtctcacag    1440
gaacccgtgc tgtttagcac aactatcgcc gagaatattt gttatggtag aggcaacgtg    1500
acaatggatg aaattaagaa agctgtcaag gaggctaatg catacgaatt catcatgaaa    1560
ctccctcaga gtttgatac tctggtgggc gagaggggcg cccagctgag cggggtcag    1620 aaacagcgca tcgccattgc tcgagcactg gtgaggaacc caaagatcct gctcctggac    1680
gaggccacat ccgctctgga tactgaatct gaggccgaag tgcaggccgc tctggacaag    1740
gctagggaag gcagaaccac aatcgtgatt gcccacagac tgagcaccgt gcggaatgcc    1800
gacgtgattg ctggcttcga ggatggagtg atcgtcgaac agggctccca ttctgagctg    1860
atgaagaaag aaggagtgta tttcaagctg gtcaacatgc agacaagtgg ctcacagatc    1920
cagtccgaag agtttgagct gaatgacgaa aaagcagcca aaggatggc cccaaacgga    1980 tggaagagtc ggctcttccg ccactcaact cagaagaatc tgaaaaacag ccagatgtgc    2040
cagaagtccc tcgacgtgga gaccgatggg ctggaagcta atgtgccccc tgtctccttc    2100
ctgaaggtgc tcaaactgaa caagaccgag tggccctact tgtggtcgg cacagtctgc    2160 gccatcgcta atggcggact gcagcccgcc ttcagcgtga tcttcagcga aatcattgct    2220
atcttcggac tggggacga tgcagtgaaa cagcagaagt gtaacatctt tagtctgatt    2280
ttcctctttc tgggcatcat ttcattcttt acattcttc tgcagggatt cacttttgga    2340
aaggccgggg agatcctcac caggagactg aggagcatgg cattcaaagc catgctgaga    2400
caggatatgt cctggtttga cgatcataag aattctacag gcgccctcag tactagactg    2460
gctaccgacg ctgcacaggt gcagggtgca acaggcactc ggctcgctct gatcgcacag    2520
aacattgcaa atctcgggac tggaatcatt atctcctta tctatggttg gcagttaacc    2580
ctgctgctgc tggccgtggt gcccatcatt gccgtgtccg gcatcgtgga aatgaaactg    2640
ctggctggaa acgctaagag agataagaaa gaactggagg ctgctggaaa aatcgctacc    2700
gaggctattg agaacattag aaccgtggtc tctctcacac aggagcggaa gttcgaaagt    2760
atgtacgtgg agaaactgta cgggccatat cgaaacagtg tgcagaaggc ccacatctat    2820
ggtattacat tttcaatcag ccaggccttc atgtacttta gctatgctgg gtgcttccgc    2880
tttggtgcat atctgatcgt gaatggccat atgaggttca gagacgtgat cctcgtcttc    2940
agcgccatcg tgttcggagc tgtcgctctg ggacacgcca gctccttgc tcccgattac    3000 gcaaaggcca aactgtccgc cgctcatctc ttcatgctgt ttgagagaca gcctctcatc    3060
gactcctatt ctgaggaagg cctgaagcca gataaattcg agggaaacat tacattcaat    3120
gaagtggtct ttaactaccc cactcgggct aatgtgcctg tcctgcaggg actctccctg    3180
gaagtgaaga aagggcagac tctcgccctg gtcggttcta gtgggtgcgg caagtctacc    3240
gtggtccagc tgctcgagcg gttttacgac ccctggcag ggactgtgct gctcgatggt    3300
caggaagcta gaaactgaa cgtgcagtgg ctgagcac agctgggaat cgtctcacag    3360
gagcctattc tgttcgactg tagcatcgca gaaaacattg cctatggaga caatagtagg    3420
gtggtctcac aggatgagat cgtgtctgca gccaaggctg caaatatcca cccttcatc    3480 gagacactgc cccataagta cgaaactcgc gtgggcgata aggaaccca gctgagcggc    3540 ggacagaaac agcgaatcgc tattgcacga gccctgatca ggcagcccca gattctgctc    3600
```

```
ctggacgagg ctactagcgc actcgatacc gagtccgaaa aggtggtcca ggaggctctg    3660
gacaaagcac gggaaggccg cacctgtatc gtgattgccc acaggctcag cacaatccag    3720
aacgctgatc tgattgtggt cttccagaat ggcagagtga aggagcacgg aacacatcag    3780
cagctcctgg cacagaaggg aatctatttt tcaatggtct ccgtccaggc aggcactcag    3840
aatctctaa                                                             3849
```

<210> SEQ ID NO 12
<211> LENGTH: 327
<212> TYPE: DNA
<213> ORGANISM: Homo sapiens

<400> SEQUENCE: 12

```
gctcagaggc acacaggagt ttctgggctc accctgcccc cttccaaccc ctcagttccc     60
atcctccagc agctgtttgt gtgctgcctc tgaagtccac actgaacaaa cttcagccta    120
ctcatgtccc taaaatgggc aaacattgca agcagcaaac agcaaacaca cagccctccc    180
tgcctgctga ccttggagct ggggcagagg tcagagacct ctctgggccc atgccacctc    240
caacatccac tcgacccctt ggaatttcgg tggagaggag cagaggttgt cctggcgtgg    300
tttaggtagt gtgagagggt ccggcga                                        327
```

<210> SEQ ID NO 13
<211> LENGTH: 192
<212> TYPE: DNA
<213> ORGANISM: Homo sapiens

<400> SEQUENCE: 13

```
ccctaaaatg ggcaaacatt gcaagcagca aacagcaaac acacagccct ccctgcctgc     60
tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gg                                                        192
```

<210> SEQ ID NO 14
<211> LENGTH: 397
<212> TYPE: DNA
<213> ORGANISM: Homo sapiens

<400> SEQUENCE: 14

```
gatcttgcta ccagtggaac agccactaag gattctgcag tgagagcaga gggccagcta     60
agtggtactc tcccagagac tgtctgactc acgccacccc ctccaccttg acacaggac     120 gctgtggttt ctgagccagg tacaatgact cctttcggta agtgcagtgg aagctgtaca    180
ctgcccaggc aaagcgtccg ggcagcgtag gcgggcgact cagatcccag ccagtggact    240
tagcccctgt ttgctcctcc gataactggg gtgaccttgg ttaatattca ccagcagcct    300 ccccgttgc ccctctggat ccactgctta aatacgacg aggacagggc cctgtctcct      360
cagcttcagg caccaccact gacctgggac agtgaat                             397
```

<210> SEQ ID NO 15
<211> LENGTH: 254
<212> TYPE: DNA
<213> ORGANISM: Homo sapiens

<400> SEQUENCE: 15

```
aatgactcct ttcggtaagt gcagtggaag ctgtacactg cccaggcaaa gcgtccgggc     60
```

```
agcgtaggcg ggcgactcag atcccagcca gtggacttag cccctgtttg ctcctccgat      120
aactggggtg accttggtta atattcacca gcagcctccc ccgttgcccc tctggatcca      180
ctgcttaaat acggacgagg cagggccct gtctcctcag cttcaggcac caccactgac       240
ctgggacagt gaat                                                        254
```

```
<210> SEQ ID NO 16
<211> LENGTH: 589
<212> TYPE: DNA
<213> ORGANISM: Woodchuck hepatitis virus

<400> SEQUENCE: 16
aatcaacctc tggattacaa aatttgtgaa agattgactg gtattcttaa ctatgttgct      60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact      240 ggttggggca ttgccaccac ctgtcagctc ctttccggga ctttcgcttt ccccctccct     300
attgccacgg cggaactcat cgccgcctgc cttgcccgct gctggacagg ggctcggctg     360
ttgggcactg acaattccgt ggtgttgtcg gggaaatcat cgtcctttcc ttggctgctc     420
gcctgtgttg ccacctggat tctgcgcggg acgtccttct gctacgtccc ttcggccctc     480
aatccagcgc accttcctcc ccgcggcctg ctgccggctc tgcggcctct tccgcgtctt     540
cgccttcgcc tcagacgagt cggatctccc ctttgggccg cctccccgc                589
```

```
<210> SEQ ID NO 17
<211> LENGTH: 261
<212> TYPE: DNA
<213> ORGANISM: Bos taurus

<400> SEQUENCE: 17
tcgctgatca gcctcgactg tgccttctag ttgccagcca tctgttgttt gccccctccc      60
cgtgccttcc ttgaccctgg aaggtgccac tcccactgtc ctttcctaat aaaatgagga     120
aattgcatcg cattgtctga gtaggtgtca ttctattctg gggggtgggg tggggcagga    180
cagcaagggg gaggattggg aagacaatag caggcatgct ggggatgcgg tgggctctat    240
ggcttctgag gcggaaagaa c                                                261
```

```
<210> SEQ ID NO 18
<211> LENGTH: 134
<212> TYPE: DNA
<213> ORGANISM: Simian virus 40

<400> SEQUENCE: 18
atgctttatt tgtgaaattt gtgatgctat tgctttattt gtaaccatta taagctgcaa      60
taaacaagtt aacaacaaca attgcattca ttttatgttt caggttcagg gggaggtgtg     120
ggaggttttt taaa                                                        134
```

```
<210> SEQ ID NO 19
<211> LENGTH: 7291
<212> TYPE: DNA
<213> ORGANISM: Artificial
<220> FEATURE:
<223> OTHER INFORMATION: Synthetic sequence

<400> SEQUENCE: 19
tagctgcgcg ctcgctcgct cactgaggcc gcccgggcaa agcccgggcg tcgggcgacc      60
```

```
tttggtcgcc cggcctcagt gagcgagcga gcgcgcagag agggagtggc caactccatc    120
actaggggtt ccttgtagtt aatgattaac ccgccatgct acttatctac gtagccatgc    180
tctaggtacc gagctcttaa ttaactgcag gctcagaggc acacaggagt ttctgggctc    240
accctgcccc cttccaaccc ctcagttccc atcctccagc agctgtttgt gtgctgcctc    300
tgaagtccac actgaacaaa cttcagccta ctcatgtccc taaaatgggc aaacattgca    360
agcagcaaac agcaaacaca cagccctccc tgcctgctga ccttggagct ggggcagagg    420
tcagagacct ctctgggccc atgccacctc caacatccac tcgacccctt ggaatttcgg    480
tggagaggag cagaggttgt cctggcgtgg tttaggtagt gtgagagggt ccggcgatta    540
actgcaggct cagaggcaca caggagtttc tgggctcacc ctgccccctt ccaacccctc    600
agttcccatc ctccagcagc tgtttgtgtg ctgcctctga agtccacact gaacaaactt    660
cagcctactc atgtccctaa aatgggcaaa cattgcaagc agcaaacagc aaacacacag    720
ccctccctgc ctgctgacct tggagctggg gcagaggtca gagacctctc tgggcccatg    780
ccacctccaa catccactcg accccttgga atttcggtgg agaggagcag aggttgtcct    840
ggcgtggttt aggtagtgtg agagggtccg gcgaattaag atcttgctac cagtggaaca    900
gccactaagg attctgcagt gagagcagag ggccagctaa gtggtactct cccagagact    960
gtctgactca cgccaccccc tccaccttgg acacaggacg ctgtggtttc tgagccaggt   1020
acaatgactc ctttcggtaa gtgcagtgga agctgtacac tgcccaggca agcgtccgg   1080 gcagcgtagg cgggcgactc agatcccagc cagtggactt agccctgtt tgctcctccg   1140 ataactgggg tgaccttggt taatattcac cagcagcctc ccccgttgcc cctctggatc   1200
cactgcttaa atacggacga ggacagggcc ctgtctcctc agcttcaggc accaccactg   1260
acctgggaca gtgaatgcgg ccgctctaga actagtgccg ccaccatggg tagttcttta   1320
gacgatgagc atatcctctc tgctcttctg caaagcgatg acgagcttgt tggtgaggat   1380
tctgacagtg aaatatcaga tcacgtaagt gaagatgacg tccagagcga tacagaagaa   1440
gcgtttatag atgaggtaca tgaagtgcag ccaacgtcaa gcggtagtga aatattagac   1500
gaacaaaatg ttattgaaca accaggttct tcattggctt ctaacagaat cttgaccttg   1560
ccacagagga ctattagagg taagaataaa cattgttggt caacttcaaa gtccacgagg   1620
cgtagccgag tctctgcact gaacattgtc agatctcaaa gaggtccgac gcgtatgtgc   1680
cgcaatatat atgacccact tttatgcttc aaactatttt ttactgatga gataatttcg   1740
gaaattgtaa aatggacaaa tgctgagata tcattgaaac gtcgggaatc tatgacaggt   1800
gctacatttc gtgacacgaa tgaagatgaa atctatgctt tctttggtat tctggtaatg   1860
acagcagtga gaaaagataa ccacatgtcc acagatgacc tctttgatcg atctttgtca   1920
atggtgtacg tctctgtaat gagtcgtgat cgttttgatt ttttgatacg atgtcttaga   1980
atggatgaca aaagtatacg gcccacactt cgagaaaacg atgtatttac tcctgttaga   2040
aaaatatggg atctctttat ccatcagtgc atacaaaatt acactccagg ggctcatttg   2100
accatagatg aacagttact tggttttaga ggacggtgtc cgtttaggat gtatatccca   2160
aacaagccaa gtaagtatgg aataaaaatc ctcatgatgt gtgacagtgg tacgaagtat   2220
atgataaatg gaatgcctta tttgggaaga ggaacacaga ccaacggagt accactcggt   2280
gaatactacg tgaaggagtt atcaaagcct gtgcacggta gttgtcgtaa tattacgtgt   2340
gacaattggt tcacctcaat cccctttggca aaaaacttac tacaagaacc gtataagtta   2400
```

```
accattgtgg gaaccgtgcg atcaaacaaa cgcgagatac cggaagtact gaaaaacagt    2460
cgctccaggc cagtgggaac atcgatgttt tgttttgacg gacccctta c tctcgtctca    2520 tataaaccga agccagctaa gatggtatac ttattatcat cttgtgatga ggatgcttct    2580
atcaacgaaa gtaccggtaa accgcaaatg gttatgtatt ataatcaaac taaaggcgga    2640
gtggacacgc tagaccaaat gtgttctgtg atgacctgca gtaggaagac gaataggtgg    2700
cctatggcat tattgtacgg aatgataaac attgcctgca taaattcttt tattatatac    2760
agccataatg tcagtagcaa gggagaaaag gttcaaagtc gcaaaaaatt tatgagaaac    2820
ctttacatga gcctgacgtc atcgtttatg cgtaagcgtt tagaagctcc tactttgaag    2880
agatatttgc gcgataatat ctctaatatt ttgccaaatg aagtgcctgg tacatcagat    2940
gacagtactg aagagccagt aatgaaaaaa cgtacttact gtacttactg cccctctaaa    3000
ataaggcgaa aggcaaatgc atcgtgcaaa aaatgcaaaa aagttatttg tcgagagcat    3060
aatattgata tgtgccaaag ttgtttctga aagcttatcg ataatcaacc tctggattac    3120
aaaatttgtg aaagattgac tggtattctt aactatgttg ctccttttac gctatgtgga    3180
tacgctgctt taatgccttt gtatcatgct attgcttccc gtatggcttt cattttctcc    3240
tccttgtata aatcctggtt gctgtctctt tatgaggagt tgtggcccgt tgtcaggcaa    3300
cgtggcgtgg tgtgcactgt gtttgctgac gcaaccccca ctggttgggg cattgccacc    3360
acctgtcagc tcctttccgg acttttcgct ttccccctcc ctattgccac ggcggaactc    3420
atcgccgcct gccttgcccg ctgctggaca ggggctcggc tgttgggcac tgacaattcc    3480
gtggtgttgt cggggaaatc atcgtccttt ccttggctgc tcgcctgtgt tgccacctgg    3540
attctgcgcg ggacgtcctt ctgctacgtc ccttcggccc tcaatccagc ggaccttcct    3600
tcccgcggcc tgctgccggc tctgcggcct cttccgcgtc ttcgccttcg ccctcagacg    3660
agtcggatct ccctttgggc cgcctccccg catcgatacc gtcgactcgc tgatcagcct    3720
cgactgtgcc ttctagttgc cagccatctg ttgtttgccc ctcccccgtg ccttccttga    3780
ccctggaagg tgccactccc actgtccttt cctaataaaa tgaggaaatt gcatcgcatt    3840
gtctgagtag tgtcattct attctggggg gtggggtggg gcaggacagc aaggggga gg    3900 attgggaaga caatagcagg catgctgggg atgcggtggg ctctatggct tctgaggcgg    3960
aaagaaccag ctggggctcg actagagcat ggctacgtag ataagtagca tggcgggtta    4020
atcattaact acaaggaacc cctagtgatg gagttggcca ctccctctct gcgcgctcgc    4080
tcgctcactg aggccgggcg accaaaggtc gcccgacgcc cgggctttgc ccgggcggcc    4140
tcagtgagcg agcgagcgcg cagagctttt tgcaaaagcc taggcctcca aaaaagcctc    4200
ctcactactt ctggaatagc tcagaggccg aggcggcctc ggcctctgca taataaaaa    4260 aaattagtca gccatggggc ggagaatggg cggaactggg cggagttagg ggcgggatgg    4320
gcggagttag gggcgggact atggttgctg actaattgag atgcatgctt tgcatacttc    4380
tgcctgctgg ggagcctggg gactttccac acctggttgc tgactaattg agatgcatgc    4440
tttgcatact tctgcctgct ggggagcctg ggactttcc acaccctaac tgacacacat    4500
tccacagctg cattaatgaa tcggccaacg cgcggggaga ggcggtttgc gtattgggcg    4560
ctcttccgct tcctcgctca ctgactcgct gcgctcggtc gttcggctgc ggcgagcggt    4620
atcagctcac tcaaaggcgg taatacggtt atccacagaa tcaggggata acgcaggaaa    4680
gaacatgtga gcaaaaggcc agcaaaaggc caggaaccgt aaaaaggccg cgttgctggc    4740
gtttttccat aggctccgcc cccctgacga gcatcacaaa aatcgacgct caagtcagag    4800
```

```
gtggcgaaac ccgacaggac tataaagata ccaggcgttt cccccctggaa gctccctcgt    4860 gcgctctcct gttccgaccc tgccgcttac cggatacctg tccgcctttc tcccttcggg    4920
aagcgtggcg cttcctcata gctcacgctg taggtatctc agttcggtgt aggtcgttcg    4980
ctccaagctg ggctgtgtgc acgaaccccc cgttcagccc gaccgctgcg ccttatccgg    5040
taactatcgt cttgagtcca acccggtaag acacgactta tcgccactgg cagcagccac    5100
tggtaacagg attagcagag cgaggtatgt aggcggtgct acagagttct tgaagtggtg    5160
gcctaactac ggctacacta agaacagt atttggtatc tgcgctctgc tgaagccagt    5220
taccttcgga aaaagagttg gtagctcttg atccggcaaa caaaccaccg ctggtagcgg    5280
tggttttttt gtttgcaagc agcagattac gcgcagaaaa aaggatctc aagaagatcc    5340 tttgatcttt tctacggggt ctgacgctca gtggaacgaa aactcacgtt aagggatttt    5400
ggtcatgaga ttatcaaaaa ggatcttcac ctagatcctt ttaaattaaa aatgaagttt    5460
taaatcaatc taaagtatat atgagtaaac ttggtctgac agttaccaat gcttaatcag    5520
tgaggcacct atctcagcga tctgtctatt tcgttcatcc atagttgcct gactccccgt    5580
cgtgtagata actacgatac gggagggctt accatctggc cccagtgctg caatgatacc    5640
gcgagaccca cgctcaccgg ctccagattt atcagcaata accagccag ccggaagggc    5700 cgagcgcaga agtggtcctg caactttatc cgcctccatc cagtctatta attgttgccg    5760
ggaagctaga gtaagtagtt cgccagttaa tagtttgcgc aacgttgttg ccattgctac    5820
aggcatcgtg gtgtcacgct cgtcgtttgg tatggcttca ttcagctccg gttcccaacg    5880
atcaaggcga gttacatgat cccccatgtt gtgcaaaaaa gcggttagct ccttcggtcc    5940
tccgatcgtt gtcagaagta agttggccgc agtgttatca ctcatggtta tggcagcact    6000
gcataattct cttactgtca tgccatccgt aagatgcttt tctgtgactg gtgagtactc    6060
aaccaagtca ttctgagaat agtgtatgcg gcgaccgagt tgctcttgcc cggcgtcaat    6120
acgggataat accgcgccac atagcagaac tttaaaagtg ctcatcattg gaaaacgttc    6180
ttcggggcga aaactctcaa ggatcttacc gctgttgaga tccagttcga tgtaacccac    6240
tcgtgcaccc aactgatctt cagcatcttt tactttcacc agcgtttctg ggtgagcaaa    6300
aacaggaagg caaaatgccg caaaaaaggg aataagggcg acacggaaat gttgaatact    6360
catactcttc ctttttcaat attattgaag catttatcag ggttattgtc tcatgagcgg    6420
atacatattt gaatgtattt agaaaaataa acaaataggg gttccgcgca catttccccg    6480
aaaagtgcca cctgacgtct aagaaaccat tattatcatg acattaacct ataaaaatag    6540
gcgtatcacg aggccctttc gtctcgcgcg tttcggtgat gacggtgaaa acctctgaca    6600
catgcagctc ccggagacgg tcacagcttg tctgtaagcg gatgccggga gcagacaagc    6660
ccgtcagggc gcgtcagcgg gtgttggcgg gtgtcggggc tggcttaact atgcggcatc    6720
agagcagatt gtactgagag tgcaccattc gacgctctcc cttatgcgac tcctgcatta    6780
ggaagcagcc cagtagtagg ttgaggccgt tgagcaccgc cgccgcaagg aatggtgcat    6840
gcaaggagat ggcgcccaac agtccccggg ccacggggcc tgccaccata cccacgccga    6900
aacaagcgct catgagcccg aagtggcgag cccgatcttc cccatcggtg atgtcggcga    6960
tataggcgcc agcaaccgca cctgtggcgc cggtgatgcc ggccacgatg cgtccggcgt    7020
agaggatctg gctagcgatg accctgctga ttggttcgct gaccatttcc gggtgcggga    7080
cggcgttacc agaaactcag aaggttcgtc caaccaaacc gactctgacg gcagtttacg    7140
```

| | |
|---|---:|
| agagagatga tagggtctgc ttcagtaagc cagatgctac acaattaggc ttgtacatat | 7200 |
| tgtcgttaga acgcggctac aattaataca taaccttatg tatcatacac atacgattta | 7260 |
| ggtgacacta tagaatacac ggaattaatt c | 7291 |

<210> SEQ ID NO 20
<211> LENGTH: 6813
<212> TYPE: DNA
<213> ORGANISM: Artificial
<220> FEATURE:
<223> OTHER INFORMATION: Synthetic sequence

<400> SEQUENCE: 20

| | |
|---|---:|
| tagctgcgcg ctcgctcgct cactgaggcc gcccgggcaa agcccgggcg tcgggcgacc | 60 |
| tttggtcgcc cggcctcagt gagcgagcga gcgcgcagag agggagtggc caactccatc | 120 |
| actagggggtt ccttgtagtt aatgattaac ccgccatgct acttatctac gtagccatgc | 180 |
| tctagcgatc gcttaaccct agaaagatag tctgcgtaaa attgacgcat gcattcttga | 240 |
| aatattgctc tctctttcta aatagcgcga atccgtcgct gtgcatttag acatctcag | 300 |
| tcgccgcttg gagctcccgt gaggcgtgct tgtcaatgcg gtaagtgtca ctgattttga | 360 |
| actataacga ccgcgtgagt caaaatgacg catgattatc ttttacgtga cttttaagat | 420 |
| ttaactcata cgataattat attgttattt catgttctac ttacgtgata acttattata | 480 |
| tatatatttt cttgttatag atatcttaat taactgcagg ctcagaggca cacaggagtt | 540 |
| tctgggctca ccctgccccc ttccaacccc tcagttccca tcctccagca gctgtttgtg | 600 |
| tgctgcctct gaagtccaca ctgaacaaac ttcagcctac tcatgtccct aaaatgggca | 660 |
| aacattgcaa gcagcaaaca gcaaacacac agccctccct gcctgctgac cttggagctg | 720 |
| ggcagaggt cagagacctc tctgggccca tgccacctcc aacatccact cgacccttg | 780 |
| gaatttcggt ggagaggagc agaggttgtc ctggcgtggt ttaggtagtg tgagagggtc | 840 |
| cggcgattaa ctgcaggctc agaggcacac aggagtttct gggctcaccc tgccccttc | 900 |
| caaccctca gttcccatcc tccagcagct gtttgtgtgc tgcctctgaa gtccacactg | 960 |
| aacaaacttc agcctactca tgtccctaaa atgggcaaac attgcaagca gcaaacagca | 1020 |
| aacacacagc cctccctgcc tgctgacctt ggagctgggg cagaggtcag agacctctct | 1080 |
| gggcccatgc cacctccaac atccactcga ccccttggaa tttcggtgga gaggagcaga | 1140 |
| ggttgtcctg gcgtggttta ggtagtgtga gagggtccgg cgaattaaga tcttgctacc | 1200 |
| agtggaacag ccactaagga ttctgcagtg agagcagagg gccagctaag tggtactctc | 1260 |
| ccagagactg tctgactcac gccaccccct ccaccttgga cacaggacgc tgtggtttct | 1320 |
| gagccaggta caatgactcc tttcggtaag tgcagtggaa gctgtacact gcccaggcaa | 1380 |
| agcgtccggg cagcgtaggc gggcgactca gatcccagcc agtggactta gcccctgttt | 1440 |
| gctcctccga taactggggt gaccttggtt aatattcacc agcagcctcc cccgttgccc | 1500 |
| ctctggatcc actgcttaaa tacgacgag acagggccc tgtctcctca gcttcaggca | 1560 |
| ccaccactga cctgggacag tgaatgcggc cgctctagaa ctagtggatc ccccgggctg | 1620 |
| caggaattca ctagtgattt cgccgccacc atggtgagca agggcgagga gctgttcacc | 1680 |
| ggggtggtgc ccatcctggt cgagctggac ggcgacgtaa acggccacaa gttcagcgtg | 1740 |
| tccggcgagg gcgagggcga tgccacctac ggcaagctga ccctgaagtt catctgcacc | 1800 |
| accggcaagc tgcccgtgcc ctggcccacc ctcgtgacca ccctgaccta cggcgtgcag | 1860 |
| tgcttcagcc gctaccccga ccacatgaag cagcacgact tcttcaagtc cgccatgccc | 1920 |

-continued

```
gaaggctacg tccaggagcg caccatcttc ttcaaggacg acggcaacta caagacccgc    1980
gccgaggtga agttcgaggg cgacaccctg gtgaaccgca tcgagctgaa gggcatcgac    2040
ttcaaggagg acggcaacat cctggggcac aagctggagt acaactacaa cagccacaac    2100
gtctatatca tggccgacaa gcagaagaac ggcatcaagg tgaacttcaa gatccgccac    2160
aacatcgagg acggcagcgt gcagctcgcc gaccactacc agcagaacac ccccatcggc    2220
gacggccccg tgctgctgcc cgacaaccac tacctgagca cccagtccgc cctgagcaaa    2280
gaccccaacg agaagcgcga tcacatggtc ctgctggagt tcgtgaccgc cgccgggatc    2340
actctcggca tggacgagct gtacaagtaa gatatcaagc ttatcgataa tcaacctctg    2400
gattacaaaa tttgtgaaag attgactggt attcttaact atgttgctcc ttttacgcta    2460
tgtggatacg ctgctttaat gcctttgtat catgctattg cttcccgtat ggctttcatt    2520
ttctcctcct tgtataaatc ctggttgctg tctctttatg aggagttgtg gcccgttgtc    2580
aggcaacgtg gcgtggtgtg cactgtgttt gctgacgcaa ccccactggt tggggcatt     2640
gccaccacct gtcagctcct ttccgggact ttcgctttcc cctccctat  gccacggcg     2700
gaactcatcg ccgcctgcct tgcccgctgc tggacagggg ctcggctgtt gggcactgac    2760
aattccgtgg tgttgtcggg gaaatcatcg tcctttcctt ggctgctcgc ctgtgttgcc    2820
acctggattc tgcgcgggac gtccttctgc tacgtccctt cggccctcaa tccagcggac    2880
cttccttccc gcggcctgct gccggctctg cggcctcttc cgcgtcttcg ccttcgccct    2940
cagacgagtc ggatctcccT ttgggccgcc tccccgcatc gataccgtcg actcgctgat    3000
cagcctcgac tgtgccttct agttgccagc catctgttgt ttgcccctcc cccgtgcctt    3060
ccttgaccct ggaaggtgcc actcccactg tcctttccta ataaaatgag gaaattgcat    3120
cgcattgtct gagtaggtgt cattctattc tggggggtgg ggtggggcag gacagcaagg    3180
gggaggattg ggaagacaat agcaggcatg ctggggatgc ggtgggctct atggcttctg    3240
aggcggaaag aacggccggc cttTgttact ttatagaaga aattttgagt ttTtgttttT    3300
ttttaataaa taaataaaca taaataaatT gtttgttgaa tttattatta gtatgtaagt    3360
gtaaatataa taaaacttaa tatctattca aattaataaa taaacctcga tatacagacc    3420
gataaaacac atgcgtcaat tttacgcatg attatcttta acgtacgtca caatatgatt    3480
atctttctag ggttaacctg caggtagagc atggctacgt agataagtag catggcgggt    3540
taatcattaa ctacaaggaa cccctagtga tggagttggc cactccctct ctgcgcgctc    3600
gctcgctcac tgaggccggg cgaccaaagg tcgcccgacg cccgggcttt gcccgggcgg    3660
cctcagtgag cgagcgagcg cgcagagctt tttgcaaaag cctaggcctc caaaaaagcc    3720
tcctcactac ttctggaata gctcagaggc cgaggcggcc tcggcctctg cataaataaa    3780
aaaaattagt cagccatggg gcggagaatg ggcggaactg ggcggagtta ggggcgggat    3840
gggcggagtt aggggcggga ctatggttgc tgactaattg agatgcatgc tttgcatact    3900
tctgcctgct ggggagcctg gggactttcc acacctggtt gctgactaat tgagatgcat    3960
gctttgcata cttctgcctg ctggggagcc tggggacttt ccacacccta actgacacac    4020
attccacagc tgcattaatg aatcggccaa cgcgcgggga gaggcggttt gcgtattggg    4080
cgctcttccg cttcctcgct cactgactcg ctgcgctcgg tcgttcggct gcggcgagcg    4140
gtatcagctc actcaaaggc ggtaatacgg ttatccacag aatcagggga taacgcagga    4200
aagaacatgt gagcaaaagg ccagcaaaag gccaggaacc gtaaaaaggc cgcgttgctg    4260
```

```
gcgttttttcc ataggctccg ccccccctgac gagcatcaca aaaatcgacg ctcaagtcag    4320
aggtggcgaa acccgacagg actataaaga taccaggcgt ttcccctgg aagctccctc      4380 gtgcgctctc ctgttccgac cctgccgctt accggatacc tgtccgcctt tctcccttcg     4440
ggaagcgtgg cgcttctctca tagctcacgc tgtaggtatc tcagttcggt gtaggtcgtt    4500
cgctccaagc tgggctgtgt gcacgaaccc cccgttcagc ccgaccgctg cgccttatcc     4560
ggtaactatc gtcttgagtc caacccggta agacacgact tatcgccact ggcagcagcc     4620
actggtaaca ggattagcag agcgaggtat gtaggcggtg ctacagagtt cttgaagtgg    4680
tggcctaact acggctacac tagaagaaca gtatttggta tctgcgctct gctgaagcca   4740
gttaccttcg gaaaaagagt tggtagctct tgatccggca acaaaccac cgctggtagc     4800 ggtggttttt ttgtttgcaa gcagcagatt acgcgcagaa aaaaaggatc tcaagaagat   4860
cctttgatct tttctacggg gtctgacgct cagtggaacg aaaactcacg ttaagggatt    4920
ttggtcatga gattatcaaa aaggatcttc acctagatcc ttttaaatta aaaatgaagt    4980
tttaaatcaa tctaaagtat atatgagtaa acttggtctg acagttacca atgcttaatc    5040
agtgaggcac ctatctcagc gatctgtcta tttcgttcat ccatagttgc ctgactcccc   5100
gtcgtgtaga taactacgat acgggagggc ttaccatctg gccccagtgc tgcaatgata    5160
ccgcgagacc cacgctcacc ggctccagat ttatcagcaa taaaccagcc agccggaagg   5220
gccgagcgca gaagtggtcc tgcaacttta tccgcctcca tccagtctat taattgttgc   5280
cgggaagcta gagtaagtag ttcgccagtt aatagtttgc gcaacgttgt tgccattgct   5340
acaggcatcg tggtgtcacg ctcgtcgttt ggtatggctt cattcagctc cggttcccaa    5400
cgatcaaggc gagttacatg atcccccatg ttgtgcaaaa aagcggttag ctccttcggt    5460
cctccgatcg ttgtcagaag taagttggcc gcagtgttat cactcatggt tatggcagca    5520
ctgcataatt ctcttactgt catgccatcc gtaagatgct tttctgtgac tggtgagtac    5580
tcaaccaagt cattctgaga atagtgtatg cggcgaccga gttgctcttg cccggcgtca    5640
atacgggata taccgcgcc acatagcaga actttaaaag tgctcatcat tggaaaacgt    5700
tcttcggggc gaaaactctc aaggatctta ccgctgttga gatccagttc gatgtaaccc    5760
actcgtgcac ccaactgatc ttcagcatct tttactttca ccagcgtttc tgggtgagca    5820
aaaacaggaa ggcaaaatgc cgcaaaaaag ggaataaggg cgacacggaa atgttgaata    5880
ctcatactct tcctttttca atattattga agcatttatc agggttattg tctcatgagc    5940
ggatacatat ttgaatgtat ttagaaaaat aaacaaatag gggttccgcg cacatttccc    6000
cgaaaagtgc cacctgacgt ctaagaaacc attattatca tgacattaac ctataaaaat    6060
aggcgtatca cgaggccctt tcgtctcgcg cgtttcggtg atgacggtga aaacctctga    6120
cacatgcagc tcccggagac ggtcacagct tgtctgtaag cggatgccgg gagcagacaa    6180
gcccgtcagg gcgcgtcagc gggtgttggc gggtgtcggg gctggcttaa ctatgcggca    6240
tcagagcaga ttgtactgag agtgcaccat tcgacgctct cccttatgcg actcctgcat    6300
taggaagcag cccagtagta ggttgaggcc gttgagcacc gccgccgcaa ggaatggtgc    6360
atgcaaggag atggcgccca acagtccccc ggccacgggg cctgccacca tacccacgcc    6420
gaaacaagcg ctcatgagcc cgaagtggcg agcccgatct tccccatcgg tgatgtcggc    6480
gatataggcg ccagcaaccg cacctgtggc gccggtgatg ccggccacga tcgtccggc    6540 gtagaggatc tggctagcga tgaccctgct gattggttcg ctgaccattt ccgggtgcgg    6600
gacggcgtta ccagaaactc agaaggttcg tccaaccaaa ccgactctga cggcagttta    6660
```

<210> SEQ ID NO 21
<211> LENGTH: 7147
<212> TYPE: DNA
<213> ORGANISM: Artificial
<220> FEATURE:
<223> OTHER INFORMATION: Synthetic sequence
<220> FEATURE:
<221> NAME/KEY: misc_feature
<222> LOCATION: (1894)..(1894)
<223> OTHER INFORMATION: n is a, c, g, or t

<400> SEQUENCE: 21

```
cgagagagat gatagggtct gcttcagtaa gccagatgct acacaattag gcttgtacat    6720
attgtcgtta aacgcggct acaattaata cataaccta tgtatcatac acatacgatt    6780
taggtgacac tatagaatac acggaattaa ttc                                 6813 tagctgcgcg ctcgctcgct cactgaggcc gcccgggcaa agcccggcg tcgggcgacc     60
tttggtcgcc cggcctcagt gagcgagcga gcgcgcagag agggagtggc caactccatc    120
actagggtt ccttgtagtt aatgattaac ccgccatgct acttatctac gtagccatgc    180
tctagcgatc gcttaaccct agaaagatag tctgcgtaaa attgacgcat gcattcttga    240
aatattgctc tctctttcta aatagcgcga atccgtcgct gtgcatttag gacatctcag    300
tcgccgcttg gagctcccgt gaggcgtgct tgtcaatgcg gtaagtgtca ctgattttga    360
actataacga ccgcgtgagt caaaatgacg catgattatc ttttacgtga cttttaagat    420
ttaactcata cgataattat attgttattt catgttctac ttacgtgata acttattata    480
tatatatttt cttgttatag atatcttaat taactgcagg ctcagaggca cacaggagtt    540
tctgggctca ccctgccccc ttccaacccc tcagttccca tcctccagca gctgtttgtg    600
tgctgcctct gaagtccaca ctgaacaaac ttcagcctac tcatgtccct aaaatgggca    660
aacattgcaa gcagcaaaca gcaaacacac agccctccct gcctgctgac cttggagctg    720
gggcagaggt cagagacctc tctgggccca tgccacctcc aacatccact cgacccctg    780
gaatttcggt ggagaggagc agaggttgtc ctggcgtggt ttaggtagtg tgagagggtc    840
cggcgattaa ctgcaggctc agaggcacac aggagtttct gggctcaccc tgcccccttc    900
caaccctca gttcccatcc tccagcagct gtttgtgtgc tgcctctgaa gtccacactg    960
aacaaacttc agcctactca tgtcctaaa atgggcaaac attgcaagca gcaaacagca    1020
aacacacagc cctccctgcc tgctgacctt ggagctgggg cagaggtcag agacctctct    1080
gggcccatgc cacctccaac atccactcga ccccttggaa tttcggtgga gaggagcaga    1140
ggttgtcctg gcgtggttta ggtagtgtga gagggtccgg cgaattaaga tcttgctacc    1200
agtggaacag ccactaagga ttctgcagtg agagcagagg gccagctaag tggtactctc    1260
ccagagactg tctgactcac gccacccct ccaccttgga cacaggacgc tgtggtttct    1320
gagccaggta caatgactcc tttcggtaag tgcagtggaa gctgtacact gcccaggcaa    1380
agcgtccggg cagcgtaggc gggcgactca gatcccagcc agtggactta gccctgtttt    1440
gctcctccga taactggggt gaccttggtt aatattcacc agcagcctcc cccgttgccc    1500
ctctggatcc actgcttaaa tacgacgag gacagggcc tgtctcctca gcttcaggca    1560
ccaccactga cctgggacag tgaatgcggc cgctctagaa ctagtggatc cccgggctg    1620
caggaattcg ccgccaccat gctgtctaat ttgaggatcc tgctcaacaa tgcagctctt    1680
agaaagggtc acacttctgt ggttcgacat ttttggtgtg ggaagccagt ccaaagtcaa    1740
```

```
gtacagctga aaggccgtga cctcctcacc ttgaagaact tcacaggaga ggagattcag    1800
tacatgctat ggctctctgc agatctgaaa ttcaggatca agcagaaagg agaatattta    1860
cctttattgc aagggaaatc cttaggaatg attntttgag aaaagaagta ctcgaacaag    1920
actgtccaca gaaacaggct ttgctctgct gggaggacac ccttcctttc ttaccacaca    1980
agacattcac ttgggtgtga atgaaagtct cacagacacc gctcgtgtct tatctagcat    2040
gacagatgca gtgttagctc gagtgtataa acaatcagat ctggacaccc tggctaaaga    2100
agcatccatc ccaattgtca atggactgtc agacttgtat catcctatcc agatcctggc    2160
tgattacctt acactccagg aacactatgg ctctctcaaa ggtcttaccc tcagctggat    2220
aggggatggg aacaatatct tgcactctat catgatgagt gctgcaaaat tcgggatgca    2280
ccttcaagca gctactccaa agggttatga gccagatcct aatatagtca agctagcaga    2340
gcagtatgcc aaggagaatg gtaccaagtt gtcaatgaca aatgatccac tggaagcagc    2400
acgtggaggc aatgtattaa ttacagatac ttggataagc atgggacaag aggatgagaa    2460
gaaaaagcgt cttcaagctt tccaaggtta ccaggttacg atgaagactg ccaaagtggc    2520
tgcgtctgac tggacatttt tacactgttt gcctagaaag ccagaagaag tggatgatga    2580 agtatttat tctccacggt cattagtgtt cccagaggca gagaatagaa agtggacaat    2640
catggctgtc atggtatccc tgctgacaga ctactcacct gtgctccaga agccaaagtt    2700
ttgagatatc aagcttatcg ataatcaacc tctggattac aaaatttgtg aaagattgac    2760
tggtattctt aactatgttg ctccttttac gctatgtgga tacgctgctt taatgccttt    2820
gtatcatgct attgcttccc gtatggcttt cattttctcc tccttgtata atcctggtt    2880 gctgtctctt tatgaggagt tgtggcccgt tgtcaggcaa cgtggcgtgg tgtgcactgt    2940
gtttgctgac gcaaccccca ctggttgggg cattgccacc acctgtcagc tcctttccgg    3000
gactttcgct ttccccctcc ctattgccac ggcggaactc atcgccgcct gccttgcccg    3060
ctgctggaca ggggctcggc tgttgggcac tgacaattcc gtggtgttgt cggggaaatc    3120
atcgtccttt ccttggctgc tcgcctgtgt tgccacctgg attctgcgcg gacgtccttt    3180
ctgctacgtc ccttccggccc tcaatccagc ggaccttcct tcccgcggcc tgctgccggc    3240
tctgcggcct cttccgcgtc ttcgccttcg ccctcagacg agtcggatct ccctttgggc    3300
cgcctccccg catcgatacc gtcgactcgc tgatcagcct cgactgtgcc ttctagttgc    3360
cagccatctg ttgtttgccc ctcccccgtg ccttccttga ccctggaagg tgccactccc    3420
actgtccttt cctaataaaa tgaggaaatt gcatcgcatt gtctgagtag gtgtcattct    3480
attctggggg gtggggtggg gcaggacagc aaggggagg attgggaaga caatagcagg    3540
catgctgggg atgcggtggg ctctatggct tctgaggcgg aaagaacggc cggcctttgt    3600
tactttatag aagaaatttt gagttttgt ttttttttaa taaataaata aacataaata    3660
aattgtttgt tgaatttatt attagtatgt aagtgtaaat ataataaaac ttaatatcta    3720
ttcaaattaa taaataaacc tcgatataca gaccgataaa acacatgcgt caattttacg    3780
catgattatc tttaacgtac gtcacaatat gattatcttt ctagggttaa cctgcaggta    3840
gagcatggct acgtagataa gtagcatggc gggttaatca ttaactacaa ggaaccccta    3900
gtgatggagt tggccactcc ctctctgcgc gctcgctcgc tcactgaggc cgggcgacca    3960
aaggtcgccc gacgcccggg ctttgcccgg gcggcctcag tgagcgagcg agcgcgcaga    4020 gcttttgca aaagcctagg cctccaaaaa agcctcctca ctacttctgg aatagctcag    4080
aggccgaggc ggcctcggcc tctgcataaa taaaaaaat tagtcagcca tggggcggag    4140
```

```
aatgggcgga actgggcgga gttaggggcg ggatgggcgg agttaggggc gggactatgg    4200
ttgctgacta attgagatgc atgctttgca tacttctgcc tgctggggag cctggggact    4260
ttccacacct ggttgctgac taattgagat gcatgctttg catacttctg cctgctgggg    4320
agcctgggga ctttccacac cctaactgac acacattcca cagctgcatt aatgaatcgg    4380
ccaacgcgcg gggagaggcg gtttgcgtat tgggcgctct tccgcttcct cgctcactga    4440
ctcgctgcgc tcggtcgttc ggctgcggcg agcggtatca gctcactcaa aggcggtaat    4500
acggttatcc acagaatcag gggataacgc aggaaagaac atgtgagcaa aaggccagca    4560
aaaggccagg aaccgtaaaa aggccgcgtt gctggcgttt ttccataggc tccgccccc    4620 tgacgagcat cacaaaaatc gacgctcaag tcagaggtgg cgaaacccga caggactata    4680
aagataccag gcgtttcccc ctggaagctc cctcgtgcgc tctcctgttc cgaccctgcc    4740
gcttaccgga tacctgtccg cctttctccc ttcgggaagc gtggcgcttt ctcatagctc    4800
acgctgtagg tatctcagtt cggtgtaggt cgttcgctcc aagctgggct gtgtgcacga    4860
accccccgtt cagcccgacc gctgcgcctt atccggtaac tatcgtcttg agtccaaccc    4920
ggtaagacac gacttatcgc cactggcagc agccactggt aacaggatta gcagagcgag    4980
gtatgtaggc ggtgctacag agttcttgaa gtggtggcct aactacggct acactagaag    5040
aacagtattt ggtatctgcg ctctgctgaa gccagttacc ttcggaaaaa gagttggtag    5100
ctcttgatcc ggcaaacaaa ccaccgctgg tagcggtggt ttttttgttt gcaagcagca    5160
gattacgcgc agaaaaaaag gatctcaaga agatcctttg atcttttcta cggggtctga    5220
cgctcagtgg aacgaaaact cacgttaagg gattttggtc atgagattat caaaaaggat    5280
cttcacctag atccttttaa attaaaaatg aagttttaaa tcaatctaaa gtatatatga    5340
gtaaacttgg tctgacagtt accaatgctt aatcagtgag gcacctatct cagcgatctg    5400
tctatttcgt tcatccatag ttgcctgact ccccgtcgtg tagataacta cgatacggga    5460
gggcttacca tctggcccca gtgctgcaat gataccgcga acccacgct caccggctcc    5520 agatttatca gcaataaacc agccagccgg aagggccgag cgcagaagtg gtcctgcaac    5580
tttatccgcc tccatccagt ctattaattg ttgccgggaa gctagagtaa gtagttcgcc    5640
agttaatagt ttgcgcaacg ttgttgccat tgctacaggc atcgtggtgt cacgctcgtc    5700
gtttggtatg gcttcattca gctccggttc ccaacgatca aggcgagtta catgatcccc    5760
catgttgtgc aaaaaagcgg ttagctcctt cggtcctccg atcgttgtca gaagtaagtt    5820
ggccgcagtg ttatcactca tggttatggc agcactgcat aattctctta ctgtcatgcc    5880
atccgtaaga tgcttttctg tgactggtga gtactcaacc aagtcattct gagaatagtg    5940
tatgcggcga ccgagttgct cttgcccggc gtcaatacgg gataataccg cgccacatag    6000
cagaacttta aaagtgctca tcattggaaa acgttcttcg gggcgaaaac tctcaaggat    6060
cttaccgctg ttgagatcca gttcgatgta acccactcgt gcacccaact gatcttcagc    6120
atcttttact ttcaccagcg tttctgggtg agcaaaaaca ggaaggcaaa atgccgcaaa    6180
aaagggaata agggcgacac ggaaatgttg aatactcata ctcttccttt ttcaatatta    6240
ttgaagcatt tatcagggtt attgtctcat gagcggatac atatttgaat gtatttagaa    6300
aaataaacaa ataggggttc cgcgcacatt tccccgaaaa gtgccacctg acgtctaaga    6360
aaccattatt atcatgacat taacctataa aaataggcgt atcacgaggc cctttcgtct    6420
cgcgcgtttc ggtgatgacg gtgaaaacct ctgacacatg cagctcccgg agacggtcac    6480
```

```
agcttgtctg taagcggatg ccgggagcag acaagcccgt cagggcgcgt cagcgggtgt    6540
tggcgggtgt cggggctggc ttaactatgc ggcatcagag cagattgtac tgagagtgca    6600
ccattcgacg ctctccctta tgcgactcct gcattaggaa gcagcccagt agtaggttga    6660
ggccgttgag caccgccgcc gcaaggaatg gtgcatgcaa ggagatggcg cccaacagtc    6720
ccccggccac ggggcctgcc accataccca cgccgaaaca agcgctcatg agcccgaagt    6780
ggcgagcccg atcttcccca tcggtgatgt cggcgatata ggcgccagca accgcacctg    6840
tggcgccggt gatgccggcc acgatgcgtc cggcgtagag gatctggcta gcgatgaccc    6900
tgctgattgg ttcgctgacc atttccgggt gcgggacggc gttaccagaa actcagaagg    6960
ttcgtccaac caaaccgact ctgacggcag tttacgagag agatgatagg gtctgcttca    7020
gtaagccaga tgctacacaa ttaggcttgt acatattgtc gttagaacgc ggctacaatt    7080
aatacataac cttatgtatc atacacatac gatttaggtg acactataga atacacgaa     7140 ttaattc                                                              7147
```

<210> SEQ ID NO 22
<211> LENGTH: 7284
<212> TYPE: DNA
<213> ORGANISM: Artificial
<220> FEATURE:
<223> OTHER INFORMATION: Synthetic sequence

<400> SEQUENCE: 22

```
tagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120 actagggtt ccttgtagtt aatgattaac ccgccatgct acttatctac gtagccatgc     180
tctagcgatc gcttaaccct agaaagatag tctgcgtaaa attgacgcat gcattcttga     240
aatattgctc tctctttcta aatagcgcga atccgtcgct gtgcatttag gacatctcag     300
tcgccgcttg gagctcccgt gaggcgtgct tgtcaatgcg gtaagtgtca ctgattttga     360
actataacga ccgcgtgagt caaaatgacg catgattatc ttttacgtga cttttaagat     420
ttaactcata cgataattat attgttattt catgttctac ttacgtgata acttattata     480
tatatatttt cttgttatag atatcttaat taactgcagg ctcagaggca cacaggagtt     540
tctgggctca ccctgcccc ttccaaccccc tcagttccca tcctccagca gctgtttgtg     600
tgctgcctct gaagtccaca ctgaacaaac ttcagcctac tcatgtccct aaaatgggca     660
aacattgcaa gcagcaaaca gcaaacacac agccctccct gcctgctgac cttggagctg     720 ggcagaggt cagagacctc tctgggccca tgccacctcc aacatccact cgacccctttg     780 gaatttcggt ggagaggagc agaggttgtc ctggcgtggt ttaggtagtg tgagagggtc     840
cggcgattaa ctgcaggctc agaggcacac aggagtttct gggctcaccc tgccccttc     900 caacccctca gttcccatcc tccagcagct gtttgtgtgc tgcctctgaa gtccacactg     960
aacaaacttc agcctactca tgtccctaaa atgggcaaac attgcaagca gcaaacagca    1020
aacacacagc cctccctgcc tgctgacctt ggagctgggg cagaggtcag agacctctct    1080
gggcccatgc cacctccaac atccactcga ccccttggaa tttcggtgga gaggagcaga    1140
ggttgtcctg gcgtggttta ggtagtgtga gagggtccgg cgaattaaga tcttgctacc    1200
agtggaacag ccactaagga ttgcagtg agagcagagg ccagctaag tggtactctc     1260 ccagagactg tctgactcac gccacccct ccaccttgga cacaggacgc tgtggttct    1320 gagccaggta caatgactcc tttcggtaag tgcagtggaa gctgtacact gcccaggcaa    1380
```

```
agcgtccggg cagcgtaggc gggcgactca gatcccagcc agtggactta gccctgttt    1440 gctcctccga taactggggt gaccttggtt aatattcacc agcagcctcc cccgttgccc   1500
ctctggatcc actgcttaaa tacgacgag  acagggccc tgtctcctca gcttcaggca   1560
ccaccactga cctgggacag tgaatgcggc gcgccgcca ccatgtccag caagggctct    1620
gtggttctgg cctacagtgg tggcctggac acctcctgca tcctcgtgtg gctgaaggaa   1680
caaggctatg atgtcatcgc ctacctggcc aacattggcc agaaggaaga ctttgaggaa   1740
gccaggaaga aggcgctgaa gcttgggggcc aaaaaggtgt tcattgagga tgtgagcaag   1800
gaatttgtgg aagagttcat ctggcctgct gtccagtcca gtgcactcta cgaggaccgc   1860
tatctcctgg gcacctctct cgccaggcct tgcatagctc gcagacaggt ggagattgcc   1920
cagcgtgaag gggccaagta tgtgtctcac ggcgccacgg gaaagggaa  tgaccaggtc   1980 cgctttgagc tcacctgcta ttcactggca ccccagatta aggtcatcgc tccctggagg   2040
atgcctgagt tttacaaccg gttcaagggc cgaaatgatc tgatggagta tgcaaagcaa   2100
cacggaatcc ccatccctgt caccccccaag agccctgga  gtatggatga aaacctcatg   2160
cacatcagct atgaggctgg gatcctggaa accccaaga  atcaagcacc tccgggtctc   2220
tacacaaaaa ctcaggaccc tgccaaagca cccaacagcc agatgtcct  tgagatagaa   2280 ttcaaaaaag gggtccctgt gaaggtgacc aacatcaaag atggcacaac ccgcaccaca   2340
tccctggaac tcttcatgta cctgaacgaa gttgcgggca agcacggagt gggtcgcatt   2400
gacatcgtgg agaaccgctt cattggaatg aagtcccgag gtatctacga ccccagca     2460 gggaccatcc tttaccacgc tcatttagac atagaggcct tcacgatgga tcgggaagta   2520
cgcaaaatca gcagggcct  gggcctcaaa ttcgcagagc tcgtatacac aggtttctgg   2580
cacagccctg aatgtgaatt tgttcgccac tgtatccaga agtcccagga gcgggtagaa   2640
gggaaggtgc aggtgtctgt cttcaagggc caagtgtaca tcctcggtcg ggagtctcca   2700 cttttcactct acaatgaaga gctggtgagc atgaacgtgc agggcgacta tgagcccatc   2760
gacgccactg gcttcatcaa tatcaactcg ctcaggctga aggagtacca tcgccttcag   2820
agcaaggtca ctgccaaata ggatatcaag cttatcgata tcaacctct  ggattacaaa   2880 atttgtgaaa gattgactgg tattcttaac tatgttgctc cttttacgct atgtggatac   2940
gctgctttaa tgcctttgta tcatgctatt gcttcccgta tggctttcat ttctcctcc    3000 ttgtataaat cctggttgct gtctctttat gaggagttgt ggcccgttgt caggcaacgt   3060
ggcgtggtgt gcactgtgtt tgctgacgca accccactg  gttgggcat  tgccaccacc   3120 tgtcagctcc tttccgggac tttcgctttc cccctcccta ttgccacggc ggaactcatc   3180
gccgcctgcc ttgcccgctg ctggacaggg gctcggctgt tgggcactga caattccgtg   3240
gtgttgtcgg ggaaatcatc gtcctttcct tggctgctcg cctgtgttgc cacctggatt   3300
ctgcgcggga cgtccttctg ctacgtccct tcggccctca atccagcgga ccttccttcc   3360
cgcggcctgc tgccggctct gcggcctctt ccgcgtcttc gccttcgccc tcagacgagt   3420
cggatctccc tttgggccgc ctccccgcat cgataccgtc gactgctga  tcagcctcga   3480 ctgtgccttc tagttgccag ccatctgttg tttgcccctc cccgtgcct  tccttgaccc   3540 tggaaggtgc cactcccact gtcctttcct aataaaatga ggaaattgca tcgcattgtc   3600
tgagtaggtg tcattctatt ctgggggtg  ggtggggca  ggacagcaag gggaggatt    3660 gggaagacaa tagcaggcat gctggggatg cggtgggctc tatggcttct gaggcggaaa   3720
```

```
gaacggccgg cctttgttac tttatagaag aaattttgag ttttttgtttt tttttaataa    3780
ataaataaac ataaataaat tgtttgttga atttattatt agtatgtaag tgtaaatata    3840
ataaaactta atatctattc aaattaataa ataaacctcg atatacagac cgataaaaca    3900
catgcgtcaa ttttacgcat gattatcttt aacgtacgtc acaatatgat tatctttcta    3960
gggttaacct gcaggtagag catggctacg tagataagta gcatggcggg ttaatcatta    4020
actacaagga accccctagtg atggagttgg ccactccctc tctgcgcgct cgctcgctca    4080
ctgaggccgg gcgaccaaag gtcgcccgac gcccgggctt tgcccgggcg gcctcagtga    4140
gcgagcgagc gcgcagagct ttttgcaaaa gcctaggcct ccaaaaaagc ctcctcacta    4200
cttctggaat agctcagagg ccgaggcggc ctcggcctct gcataaataa aaaaaattag    4260
tcagccatgg ggcggagaat gggcggaact gggcggagtt aggggcggga tgggcggagt    4320
taggggcggg actatggttg ctgactaatt gagatgcatg ctttgcatac ttctgcctgc    4380
tggggagcct ggggactttc cacacctggt tgctgactaa ttgagatgca tgctttgcat    4440
acttctgcct gctggggagc ctggggactt tccacaccct aactgacaca cattccacag    4500
ctgcattaat gaatcggcca acgcgcgggg agaggcggtt tgcgtattgg gcgctcttcc    4560
gcttcctcgc tcactgactc gctgcgctcg gtcgttcggc tgcggcgagc ggtatcagct    4620
cactcaaagg cggtaatacg gttatccaca gaatcagggg ataacgcagg aaagaacatg    4680
tgagcaaaag gccagcaaaa ggccaggaac cgtaaaaagg ccgcgttgct ggcgtttttc    4740
cataggctcc gcccccctga cgagcatcac aaaaatcgac gctcaagtca gaggtggcga    4800
aacccgacag gactataaag ataccaggcg tttccccctg gaagctccct cgtgcgctct    4860
cctgttccga ccctgccgct taccggatac ctgtccgcct ttctcccttc gggaagcgtg    4920
gcgctttctc atagctcacg ctgtaggtat ctcagttcgg tgtaggtcgt tcgctccaag    4980
ctgggctgtg tgcacgaacc ccccgttcag cccgaccgct gcgccttatc cggtaactat    5040
cgtcttgagt ccaacccggt aagacacgac ttatcgccac tggcagcagc cactggtaac    5100
aggattagca gagcgaggta tgtaggcggt gctacagagt tcttgaagtg gtggcctaac    5160
tacggctaca ctagaagaac agtatttggt atctgcgctc tgctgaagcc agttaccttc    5220
ggaaaaagag ttggtagctc ttgatccggc aaacaaacca ccgctggtag cggtggtttt    5280
tttgtttgca agcagcagat tacgcgcaga aaaaaaggat ctcaagaaga tcctttgatc    5340
ttttctacgg ggtctgacgc tcagtggaac gaaaactcac gttaagggat tttggtcatg    5400
agattatcaa aaaggatctt cacctagatc cttttaaatt aaaaatgaag ttttaaatca    5460
atctaaagta tatatgagta aacttggtct gacagttacc aatgcttaat cagtgaggca    5520
cctatctcag cgatctgtct atttcgttca tccatagttg cctgactccc cgtcgtgtag    5580
ataactacga tacgggaggg cttaccatct ggccccagtg ctgcaatgat accgcgagac    5640
ccacgctcac cggctccaga tttatcagca ataaaccagc cagccggaag ggccgagcgc    5700
agaagtggtc ctgcaacttt atccgcctcc atccagtcta ttaattgttg ccgggaagct    5760
agagtaagta gttcgccagt taatagtttg cgcaacgttg ttgccattgc tacaggcatc    5820
gtggtgtcac gctcgtcgtt tggtatggct tcattcagct ccggttccca acgatcaagg    5880
cgagttacat gatcccccat gttgtgcaaa aaagcggtta gctccttcgg tcctccgatc    5940
gttgtcagaa gtaagttggc cgcagtgtta tcactcatgg ttatggcagc actgcataat    6000
tctcttactg tcatgccatc cgtaagatgc ttttctgtga ctggtgagta ctcaaccaag    6060
tcattctgag aatagtgtat gcggcgaccg agttgctctt gcccggcgtc aatacgggat    6120
```

```
aataccgcgc cacatagcag aactttaaaa gtgctcatca ttggaaaacg ttcttcgggg    6180
cgaaaactct caaggatctt accgctgttg agatccagtt cgatgtaacc cactcgtgca    6240
cccaactgat cttcagcatc ttttactttc accagcgttt ctgggtgagc aaaaacagga    6300
aggcaaaatg ccgcaaaaaa gggaataagg gcgacacgga aatgttgaat actcatactc    6360 ttccttttc  aatattattg aagcatttat cagggttatt gtctcatgag cggatacata    6420
tttgaatgta tttagaaaaa taaacaaata ggggttccgc gcacatttcc ccgaaaagtg    6480
ccacctgacg tctaagaaac cattattatc atgacattaa cctataaaaa taggcgtatc    6540
acgaggccct ttcgtctcgc gcgtttcggt gatgacggtg aaaacctctg acacatgcag    6600
ctcccggaga cggtcacagc ttgtctgtaa gcggatgccg ggagcagaca agcccgtcag    6660
ggcgcgtcag cgggtgttgg cgggtgtcgg gctggctta  actatgcggc atcagagcag    6720
attgtactga gagtgcacca ttcgacgctc tcccttatgc gactcctgca ttaggaagca    6780
gcccagtagt aggttgaggc cgttgagcac cgccgccgca aggaatggtg catgcaagga    6840
gatggcgccc aacagtcccc cggccacggg gcctgccacc atacccacgc cgaaacaagc    6900
gctcatgagc ccgaagtggc gagcccgatc ttccccatcg tgatgtcgg  cgatataggc    6960 gccagcaacc gcacctgtgg cgccggtgat gccggccacg atgcgtccgg cgtagaggat    7020
ctggctagcg atgaccctgc tgattggttc gctgaccatt tccggtgcg  ggacggcgtt    7080 accagaaact cagaaggttc gtccaaccaa accgactctg acggcagttt acgagagaga    7140
tgatagggtc tgcttcagta agccagatgc tacacaatta ggcttgtaca tattgtcgtt    7200
agaacgcggc tacaattaat acataacctt atgtatcata cacatacgat ttaggtgaca    7260
ctatagaata cacggaatta attc                                           7284
```

<210> SEQ ID NO 23
<211> LENGTH: 8086
<212> TYPE: DNA
<213> ORGANISM: Artificial
<220> FEATURE:
<223> OTHER INFORMATION: Synthetic sequence

<400> SEQUENCE: 23

```
tagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120 actagggtt  ccttgtagtt aatgattaac ccgccatgct acttatctac gtagccatgc     180
tctaggatat cggttaaccc tagaaagata atcatattgt gacgtacgtt aaagataatc     240
atgcgtaaaa ttgacgcatg aatcactagt ccctaaaatg gcaaacatt  gcaagcagca     300 aacagcaaac acacagccct ccctgcctgc tgaccttgga gctggggcag aggtcagaga     360
cctctctggg cccatgccac ctccaacatc cactcgaccc cttggaattt cggtggagag     420
gagcagaggt tgtcctggcg tggtttaggt agtgtgagag gggaatgact cctttcggta     480
agtgcagtgg aagctgtaca ctgcccaggc aaagcgtccg gcagcgtag  gcgggcgact     540 cagatcccag ccagtggact tagccccgt ttgctcctcc gataactggg gtgaccttgg      600
ttaatattca ccagcagcct ccccgttgc  ccctctggat ccactgctta aatacggacg     660
aggacagggc cctgtctcct cagcttcagg caccaccact gacctgggac agtgaattgc     720
tctagagccg ccaccatgga cctggaggca gcaaagaatg gaaccgcatg agaccaaca      780 tcagcagagg gggacttcga actgggtatt tcaagcaagc agaagcgcaa gaaaactaag     840
```

```
accgtgaaaa tgatcggggt cctcaccctg ttccgatact ccgactggca ggataagctc    900
tttatgtctc tgggcacaat catgccatt gctcacgggt ctggtctccc tctgatgatg    960
atcgtgttcg gggagatgac cgacaaattt gtcgatacag ccggtaattt cagcttttca   1020
gtgaacttct ctctcagtct gctcaacccc ggcaagatcc tggaggaaga gatgactcgc   1080
tatgcatact attactctgg actgggagct ggggtgctgg tcgcagctta catccaggtg   1140
agtttctgga ccctggcagc tggacggcag atccgcaaaa ttcgacagaa gttcttttcat  1200
gccatcctga acaggagat tgggtggttt gacatcaatg ataccacaga actcaacacc   1260
cggctgacag acgacatcag caaaattttcc gagggtatcg gcgataaagt gggaatgttc  1320
tttcaggcag tcgccactt ctttgccgga ttcattgtcg ggtttatccg gggttggaag   1380
ctgaccctgg tcatcatggc tatttcacca atcctcgggc tgagcgccgc agtgtgggca   1440
aagatcctct ctgccttcag tgacaaagag ctggccgctt atgctaaggc aggagctgtg   1500
gctgaagagg cactgggagc aattcgaacc gtgatcgcct ttggcggaca gaataaggaa   1560
ctcgagaggt accagaaaca cctggagaac gctaaggaaa tcgggattaa gaaagctatt   1620
tccgcaaaca tctctatggg tattgctttc ctgctcatct atgcatctta cgcactcgcc   1680
ttttggtatg cagcaccct ggtcatcagc aaggagtaca ctatcggaaa tgcaatgacc    1740
gtcttctttt ctatcctgat tggggctttc agtgtgggtc aggcagcccc ctgcatcgac   1800
gctttcgcaa atgcacgcgg cgctgcatac gtgatcttcg acatcattga taacaaccct  1860
aagatcgact cattcagcga gaggggcac aaaccagata gcattaaggg taatctggaa   1920
ttcaacgacg tgcatttttc atacccctagc agagccaatg tcaagatcct gaaaggactc  1980
aacctgaaag tgcagagcgg gcagactgtg gctctggtcg gtagctccgg atgcgggaag  2040
tccactaccg tgcagctcat tcagcggctg tatgacccag atgagggcac aatcaacatt  2100
gacggacagg acatccgcaa cttcaatgtc aactacctgc gagagatcat tggcgtggtc  2160
tcacaggaac ccgtgctgtt tagcacaact atcgccgaga atatttgtta tggtagaggc  2220
aacgtgacaa tggatgaaat taagaaagct gtcaaggagg ctaatgcata cgaattcatc  2280
atgaaactcc ctcagaagtt tgatactctg gtgggcgaga ggggcgccca gctgagcggg  2340
ggtcagaaac agcgcatcgc cattgctcga gcactggtga ggaacccaaa gatcctgctc  2400
ctggacgagg ccacatccgc tctggatact gaatctgagg ccgaagtgca ggccgctctg  2460
gacaaggcta gggaaggcag aaccacaatc gtgattgccc acagactgag caccgtgcgg  2520
aatgccgacg tgattgctgg cttcgaggat ggagtgatcg tcgaacaggg ctcccattct  2580
gagctgatga agaaagaagg agtgtatttc aagctggtca acatgcagac aagtggctca  2640
cagatccagt ccgaagagtt tgagctgaat gacgaaaaag cagccacaag gatgcccca   2700
aacggatgga agagtcggct cttccgccac tcaactcaga agaatctgaa aaacagccag  2760
atgtgccaga agtccctcga cgtggagacc gatgggctgg aagctaatgt gccccctgtc  2820
tccttcctga aggtgctcaa actgaacaag accgagtggc cctactttgt ggtcggcaca  2880
gtctgcgcca tcgctaatgg cggactgcag cccgccttca gcgtgatctt cagcgaaatc  2940
attgctatct tcggacctgg gacgatgca gtgaaacagc agaagtgtaa catctttagt  3000
ctgatttttcc tctttctggg catcatttca ttctttacat tctttctgca gggattcact  3060
tttggaaagg ccggggagat cctcaccagg agactgagga gcatggcatt caaagccatg  3120
ctgagacagg atatgtcctg gtttgacgat cataagaatt ctacaggcgc cctcagtact  3180
agactggcta ccgacgctgc acaggtgcag ggtgcaacag gcactcggct cgctctgatc  3240
```

```
gcacagaaca ttgcaaatct cgggactgga atcattatct cctttatcta tggttggcag   3300
ttaaccctgc tgctgctggc cgtggtgccc atcattgccg tgtccggcat cgtggaaatg   3360
aaactgctgg ctggaaacgc taagagagat aagaaagaac tggaggctgc tggaaaaatc   3420
gctaccgagg ctattgagaa cattagaacc gtggtctctc tcacacagga gcggaagttc   3480
gaaagtatgt acgtggagaa actgtacggg ccatatcgaa acagtgtgca gaaggcccac   3540
atctatggta ttcatttttc aatcagccag gccttcatgt actttagcta tgctgggtgc   3600
ttccgctttg gtgcatatct gatcgtgaat ggccatatga ggttcagaga cgtgatcctc   3660
gtcttcagcg ccatcgtgtt cggagctgtc gctctgggac acgccagctc ctttgctccc   3720
gattacgcaa aggccaaact gtccgccgct catctcttca tgctgtttga gagacagcct   3780
ctcatcgact cctattctga ggaaggcctg aagccagata aattcgaggg aaacattaca   3840
ttcaatgaag tggtctttaa ctaccccact cgggctaatg tgcctgtcct gcagggactc   3900
tccctggaag tgaagaaagg gcagactctc gccctggtcg gttctagtgg gtgcggcaag   3960
tctaccgtgg tccagctgct cgagcggttt tacgaccccc tggcagggac tgtgctgctc   4020
gatggtcagg aagctaagaa actgaacgtg cagtggctga gagcacagct gggaatcgtc   4080
tcacaggagc ctattctgtt cgactgtagc atcgcagaaa acattgccta tggagacaat   4140
agtagggtgg tctcacagga tgagatcgtg tctgcagcca aggctgcaaa tatccacccc   4200
ttcatcgaga cactgcccca taagtacgaa actcgcgtgg gcgataaagg aacccagctg   4260
agcggcggac agaaacagcg aatcgctatt gcacgagccc tgatcaggca gccccagatt   4320
ctgctcctgg acgaggctac tagcgcactc gataccgagt ccgaaaaggt ggtccaggag   4380
gctctggaca agcacgggga aggccgcacc tgtatcgtga ttgcccacag gctcagcaca   4440
atccagaacg ctgatctgat tgtggtcttc cagaatggca gagtgaagga gcacggaaca   4500
catcagcagc cctggcaca gaagggaatc tattttttcaa tggtctccgt ccaggcaggc   4560
actcagaatc tctaaaagct tgcagttatc gatatgcttt atttgtgaaa tttgtgatgc   4620
tattgcttta tttgtaacca ttataagctg caataaacaa gttaacaaca acaattgcat   4680
tcattttatg tttcaggttc aggggggaggt gtgggaggtt ttttaaacgc gtgcatgcgt   4740
caattttacg cagactatct ttctagggtt aagcaccggt agcatggcta cgtagataag   4800
tagcatggcg ggttaatcat taactacaag gaaccctag tgatggagtt ggccactccc   4860
tctctgcgcg ctcgctcgct cactgaggcc gggcgaccaa aggtcgcccg acgcccgggc   4920
tttgcccggg cggcctcagt gagcgagcga gcgcgcagag cttttttgcaa aagcctaggc   4980 ctccaaaaaa gcctcctcac tacttctgga atagctcaga ggccgaggcg gcctcggcct   5040
ctgcataaat aaaaaaaatt agtcagccat ggggcggaga atgggcggaa ctgggcggag   5100
ttaggggcgg gatgggcgga gttaggggcg ggactatggt tgctgactaa ttgagatgca   5160
tgctttgcat acttctgcct gctgggagc ctggggactt ccacacctg gttgctgact   5220 aattgagatg catgctttgc atacttctgc ctgctgggga gcctggggac tttccacacc   5280
ctaactgaca cacattccac agctgcatta atgaatcggc caacgcgcgg ggagaggcgg   5340
tttgcgtatt gggcgctctt ccgcttcctc gctcactgac tcgctgcgct cggtcgttcg   5400
gctgcggcga gcggtatcag ctcactcaaa ggcggtaata cggttatcca cagaatcagg   5460
ggataacgca ggaaagaaca tgtgagcaaa aggccagcaa aaggccagga accgtaaaaa   5520
ggccgcgttg ctggcgtttt tccataggct ccgcccccct gacgagcatc acaaaaatcg   5580
```

```
acgctcaagt cagaggtggc gaaacccgac aggactataa agataccagg cgtttccccc    5640
tggaagctcc ctcgtgcgct ctcctgttcc gaccctgccg cttaccggat acctgtccgc    5700
ctttctccct tcgggaagcg tggcgctttc tcatagctca cgctgtaggt atctcagttc    5760
ggtgtaggtc gttcgctcca agctgggctg tgtgcacgaa ccccccgttc agcccgaccg    5820
ctgcgcctta tccggtaact atcgtcttga gtccaacccg gtaagacacg acttatcgcc    5880
actggcagca gccactggta acaggattag cagagcgagg tatgtaggcg gtgctacaga    5940
gttcttgaag tggtggccta actacggcta cactagaaga acagtatttg gtatctgcgc    6000
tctgctgaag ccagttacct tcggaaaaag agttggtagc tcttgatccg gcaaacaaac    6060
caccgctggt agcggtggtt ttttgtttg caagcagcag attacgcgca gaaaaaaagg    6120
atctcaagaa gatcctttga tcttttctac ggggtctgac gctcagtgga acgaaaactc    6180
acgttaaggg attttggtca tgagattatc aaaaaggatc ttcacctaga tccttttaaa    6240
ttaaaaatga agttttaaat caatctaaag tatatatgag taaacttggt ctgacagtta    6300
ccaatgctta atcagtgagg cacctatctc agcgatctgt ctatttcgtt catccatagt    6360
tgcctgactc cccgtcgtgt agataactac gatacgggag ggcttaccat ctggccccag    6420
tgctgcaatg ataccgcgag acccacgctc accggctcca gatttatcag caataaacca    6480
gccagccgga agggccgagc gcagaagtgg tcctgcaact ttatccgcct ccatccagtc    6540
tattaattgt tgccgggaag ctagagtaag tagttcgcca gttaatagtt tgcgcaacgt    6600
tgttgccatt gctacaggca tcgtggtgtc acgctcgtcg tttggtatgg cttcattcag    6660
ctccggttcc caacgatcaa ggcgagttac atgatccccc atgttgtgca aaaaagcggt    6720
tagctccttc ggtcctccga tcgttgtcag aagtaagttg gccgcagtgt tatcactcat    6780
ggttatggca gcactgcata attctcttac tgtcatgcca tccgtaagat gcttttctgt    6840
gactggtgag tactcaacca agtcattctg agaatagtgt atgcggcgac cgagttgctc    6900
ttgcccggcg tcaatacggg ataataccgc gccacatagc agaactttaa aagtgctcat    6960
cattggaaaa cgttcttcgg ggcgaaaact ctcaaggatc ttaccgctgt tgagatccag    7020
ttcgatgtaa cccactcgtg cacccaactg atcttcagca tcttttactt tcaccagcgt    7080
ttctgggtga gcaaaaacag gaaggcaaaa tgccgcaaaa aagggaataa gggcgacacg    7140
gaaatgttga atactcatac tcttcctttt tcaatattat tgaagcattt atcagggtta    7200
ttgtctcatg agcggataca tatttgaatg tatttagaaa aataaacaaa tagggggttcc    7260
gcgcacattt ccccgaaaag tgccacctga cgtctaagaa accattatta tcatgacatt    7320
aacctataaa aataggcgta tcacgaggcc ctttcgtctc gcgcgtttcg gtgatgacgg    7380
tgaaaacctc tgacacatgc agctcccgga gacggtcaca gcttgtctgt aagcggatgc    7440
cgggagcaga caagcccgtc agggcgcgtc agcgggtgtt ggcgggtgtc ggggctggct    7500
taactatgcg gcatcagagc agattgtact gagagtgcac cattgacgc tctcccttat    7560
gcgactcctg cattaggaag cagcccagta gtaggttgag gccgttgagc accgccgccg    7620
caaggaatgg tgcatgcaag gagatggcgc ccaacagtcc cccggccacg gggcctgcca    7680
ccatacccac gccgaaacaa gcgctcatga gcccgaagtg gcgagcccga tcttccccat    7740
cggtgatgtc ggcgatatag gcgccagcaa ccgcacctgt ggcgccggtg atgccggcca    7800
cgatgcgtcc ggcgtagagg atctggctag cgatgaccct gctgattggt tcgctgacca    7860
tttccgggtg cgggacggcg ttaccagaaa ctcagaaggt tcgtccaacc aaaccgactc    7920
tgacggcagt ttacgagaga gatgatagg tctgcttcag taagccagat gctacacaat    7980
```

```
taggcttgta catattgtcg ttagaacgcg gctacaatta atacataacc ttatgtatca    8040
tacacatacg atttaggtga cactatagaa tacacggaat taattc                  8086
```